United States Patent
Salamon et al.

(10) Patent No.: US 10,791,943 B2
(45) Date of Patent: Oct. 6, 2020

(54) SYSTEM AND METHOD FOR SYNCHRONIZING EXTERNAL COMPRESSION OF A LIMB FOR INCREASED BLOOD

(71) Applicant: PRESSION LLC, Landenberg, PA (US)

(72) Inventors: Adam C. Salamon, Landenberg, PA (US); Richard L. Hughson, Agatha (CA); Sean D. Peterson, Gadshill (CA); Chekema N. Prince, Kitchener (CA)

(73) Assignee: PRESSION LLC, Landenburg ( * ) Notice: Subject to any disclaimer, the term of this patent is extended or adjusted under 35 U.S.C. 154(b) by 178 days.

(21) Appl. No.: 15/564,054

(22) PCT Filed: Apr. 4, 2016

(86) PCT No.: PCT/US2016/025832
§ 371 (c)(1),
(2) Date: Oct. 3, 2017

(87) PCT Pub. No.: WO2016/161414
PCT Pub. Date: Oct. 6, 2016

(65) Prior Publication Data
US 2018/0098707 A1 Apr. 12, 2018

Related U.S. Application Data

(60) Provisional application No. 62/142,931, filed on Apr. 3, 2015.

(51) Int. Cl.
*A61B 5/026* (2006.01)
*A61B 5/00* (2006.01)
(Continued)

(52) U.S. Cl.
CPC ........ *A61B 5/0261* (2013.01); *A61B 5/02416* (2013.01); *A61B 5/0488* (2013.01);
(Continued)

(58) Field of Classification Search
CPC ... A61B 5/4836; A61B 5/0488; A61B 5/0205; A61B 5/026; A61H 9/0078;
(Continued)

(56) References Cited

U.S. PATENT DOCUMENTS 3,866,604 A 2/1975 Curless et al.
4,372,297 A 2/1983 Perlin
(Continued)

FOREIGN PATENT DOCUMENTS

| EP | 0 388 200 | 9/1990 |
|---|---|---|
| EP | 2 445 320 | 4/2012 |
| WO | 2010111028 | 9/2010 |

OTHER PUBLICATIONS

International Search Report, dated Jul. 4, 2016.
(Continued)

*Primary Examiner* — Sean P Dougherty
(74) *Attorney, Agent, or Firm* — Bereskin & Parr LLP/S.E.N.C.R.L.,s.r.l.

(57) ABSTRACT

Embodiments relate to devices, systems and methods of assisting blood flow return to the heart from a limb. The device comprising a wearable garment and a compression apparatus embedded in the garment for applying an external compression to a limb of a user and at least one of a processor or a controller configured to control the compression apparatus to apply the external compression, according to a compression sequence, to a muscle of the limb of the user based on real-time measurements regarding a cardiac cycle having a diastolic phase and systolic phase of the user and real-time measurements of muscle activity. The com-
(Continued)

pression sequence is synchronized to commence when both a local blood flow at the limb is in the diastolic phase and the muscle is in a non-contracted state.

20 Claims, 14 Drawing Sheets

(51) Int. Cl.
*A61B 5/024* (2006.01)
*A61B 5/0488* (2006.01)
*A61H 9/00* (2006.01)
*A61B 5/0205* (2006.01)

(52) U.S. Cl.
CPC .......... *A61B 5/4836* (2013.01); *A61B 5/6824* (2013.01); *A61B 5/6828* (2013.01); *A61H 9/0078* (2013.01); *A61B 5/0205* (2013.01); *A61B 5/026* (2013.01); *A61H 2201/1246* (2013.01); *A61H 2201/164* (2013.01); *A61H 2201/165* (2013.01); *A61H 2201/1635* (2013.01); *A61H 2201/1654* (2013.01); *A61H 2201/5007* (2013.01); *A61H 2201/5061* (2013.01); *A61H 2201/5071* (2013.01); *A61H 2201/5092* (2013.01); *A61H 2201/5097* (2013.01); *A61H 2209/00* (2013.01); *A61H 2230/04* (2013.01); *A61H 2230/045* (2013.01); *A61H 2230/06* (2013.01); *A61H 2230/08* (2013.01); *A61H 2230/25* (2013.01); *A61H 2230/255* (2013.01); *A61H 2230/30* (2013.01); *A61H 2230/60* (2013.01)

(58) Field of Classification Search
CPC .......... A61H 2201/165; A61H 2230/04; A61H 2201/5061
See application file for complete search history.

(56) References Cited

U.S. PATENT DOCUMENTS

| | | | |
|---|---|---|---|
| 5,263,473 A | 11/1993 | McWhorter | |
| 5,514,079 A | 5/1996 | Dillon | |
| 5,968,073 A | 10/1999 | Jacobs | |
| 6,893,409 B1 | 5/2005 | Lina | |
| 6,921,373 B1 | 7/2005 | Bernstein | |
| 7,048,702 B2 | 5/2006 | Hui | |
| 8,175,713 B1 | 5/2012 | Cywinski | |
| 8,197,416 B1 * | 6/2012 | Shankar | A61B 5/02233 600/492 |
| 8,246,556 B2 | 8/2012 | Mayer et al. | |
| 8,311,632 B2 | 11/2012 | Pless et al. | |
| 8,764,690 B2 | 7/2014 | Gough | |
| 2002/0026120 A1 | 2/2002 | Ogura et al. | |
| 2005/0075531 A1 * | 4/2005 | Loeb | A61H 9/0078 600/17 |
| 2005/0159690 A1 * | 7/2005 | Barak | A61H 9/0078 601/149 |
| 2006/0021261 A1 | 2/2006 | Face | |
| 2007/0173886 A1 | 7/2007 | Rousso et al. | |
| 2008/0195018 A1 | 8/2008 | Larson et al. | |
| 2009/0036938 A1 | 2/2009 | Shipley et al. | |
| 2010/0056966 A1 | 3/2010 | Toth | |
| 2010/0105993 A1 * | 4/2010 | Naghavi | A61B 5/411 600/301 |
| 2011/0040220 A1 | 2/2011 | Holgreen | |
| 2011/0066091 A1 * | 3/2011 | Larson | A61B 17/1325 601/134 |
| 2011/0214315 A1 | 9/2011 | Mayer et al. | |
| 2011/0218473 A1 | 9/2011 | Farrow et al. | |
| 2011/0313482 A1 * | 12/2011 | Dupelle | A61H 31/004 607/3 |
| 2012/0022413 A1 | 1/2012 | Mayer et al. | |
| 2012/0065561 A1 | 3/2012 | Ballas et al. | |
| 2012/0203132 A1 * | 8/2012 | Blumensohn | A61H 23/04 600/546 |
| 2013/0102939 A1 * | 4/2013 | Sudarev | A61B 5/0225 601/151 |
| 2013/0204106 A1 * | 8/2013 | Bennett | A61B 5/0022 600/324 |
| 2014/0052028 A1 * | 2/2014 | Wright | A61B 5/6824 600/592 |
| 2014/0094726 A1 | 4/2014 | Malhi et al. | |
| 2014/0358193 A1 * | 12/2014 | Lyons | A61B 5/0402 607/48 |
| 2015/0032039 A1 | 1/2015 | Farrow et al. | |
| 2015/0038888 A1 | 2/2015 | Allen et al. | |
| 2015/0257970 A1 | 9/2015 | Mucke et al. | |
| 2015/0290073 A1 * | 10/2015 | Reeves | A61H 9/0078 601/149 |
| 2016/0058644 A1 * | 3/2016 | Cheatham, III | A61B 5/1118 601/84 |
| 2016/0120733 A1 * | 5/2016 | Ishikawa | A61B 5/02438 601/151 |
| 2016/0120734 A1 * | 5/2016 | Ishikawa | A45F 3/04 601/151 |
| 2016/0220808 A1 * | 8/2016 | Hyde | A61B 5/6804 |
| 2016/0235965 A1 * | 8/2016 | Burr | A61N 1/36034 |
| 2017/0000360 A1 * | 1/2017 | Breen | A61B 5/11 |
| 2019/0083353 A1 * | 3/2019 | Khurana | A61B 5/14551 |

OTHER PUBLICATIONS

Book et al., Investigating the Impact of Passive External Lower Limb Compression on Central and Peripheral Hemodynamics During Exercise, Eur J Appl Physiol, published online Jan. 25, 2016.
Dohm et al., "Micro-Mobile Foot Compression Device Compared with Pneumatic Compression Device," Clin Orthop Relat Res (2011), published online Mar. 15, 2011.

* cited by examiner

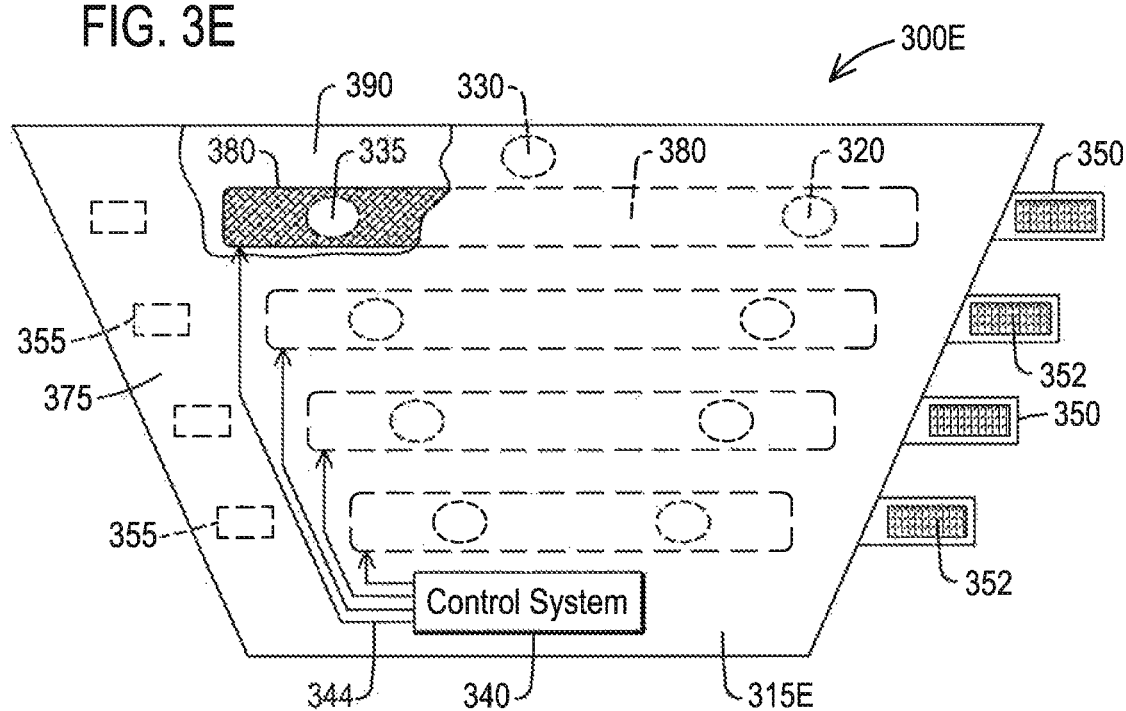
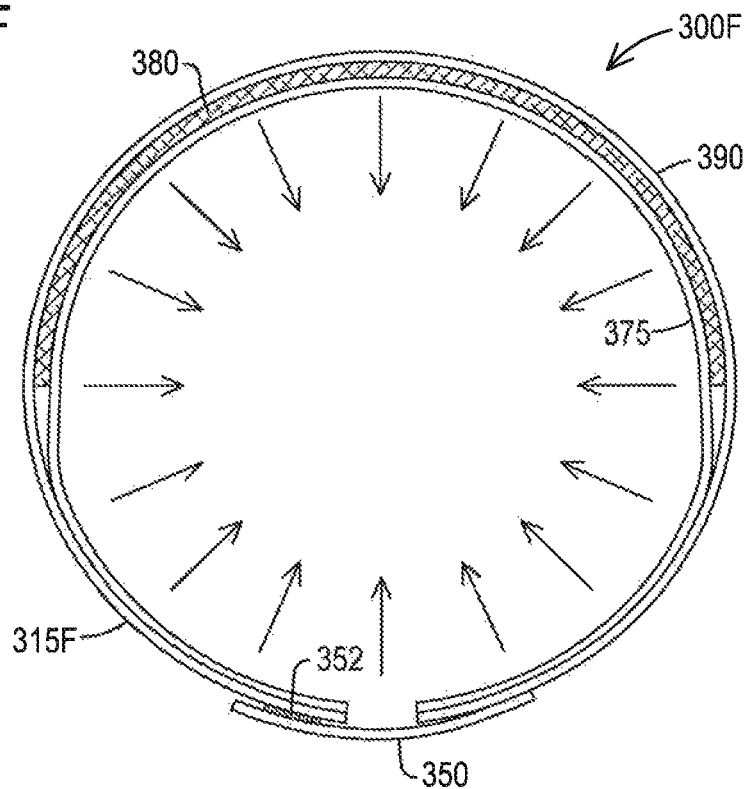

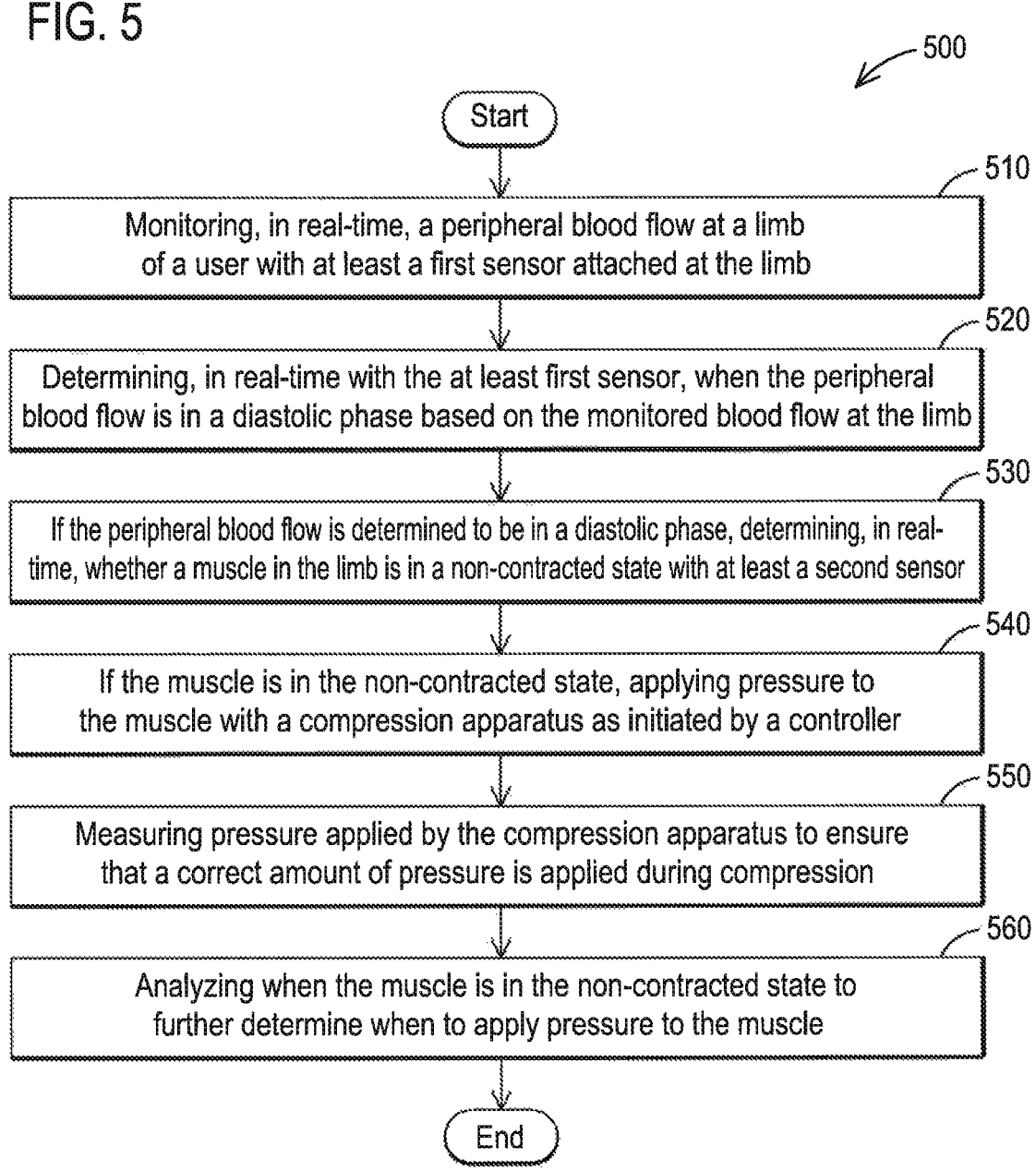

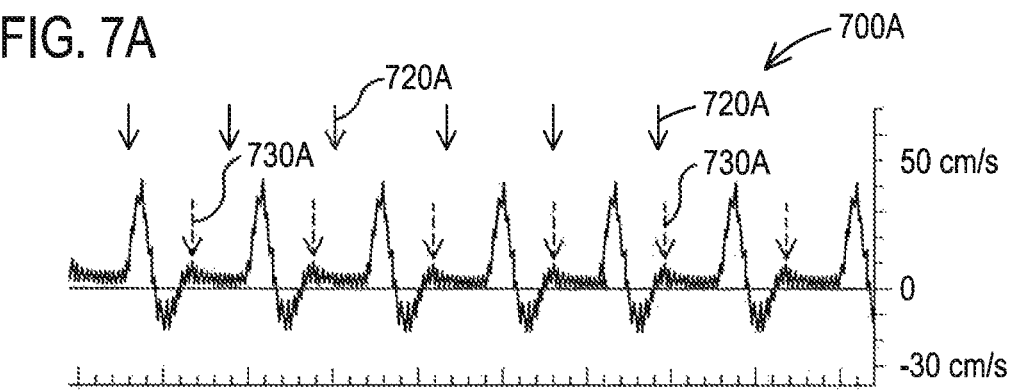
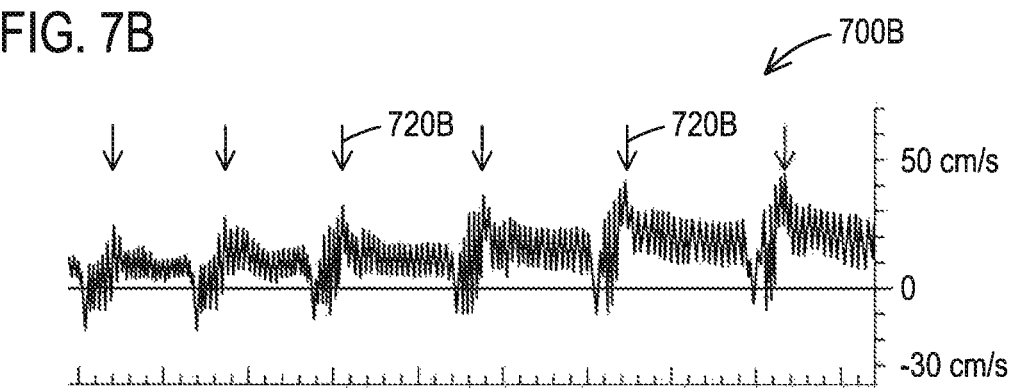
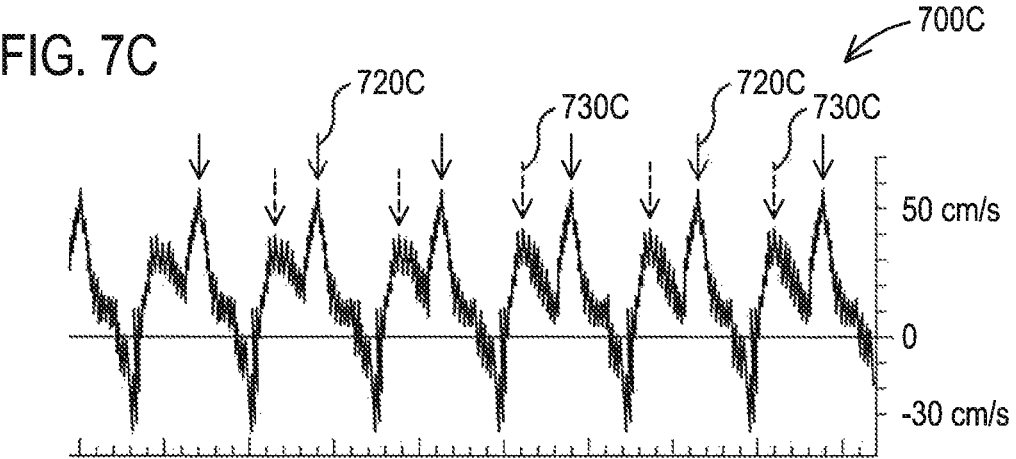

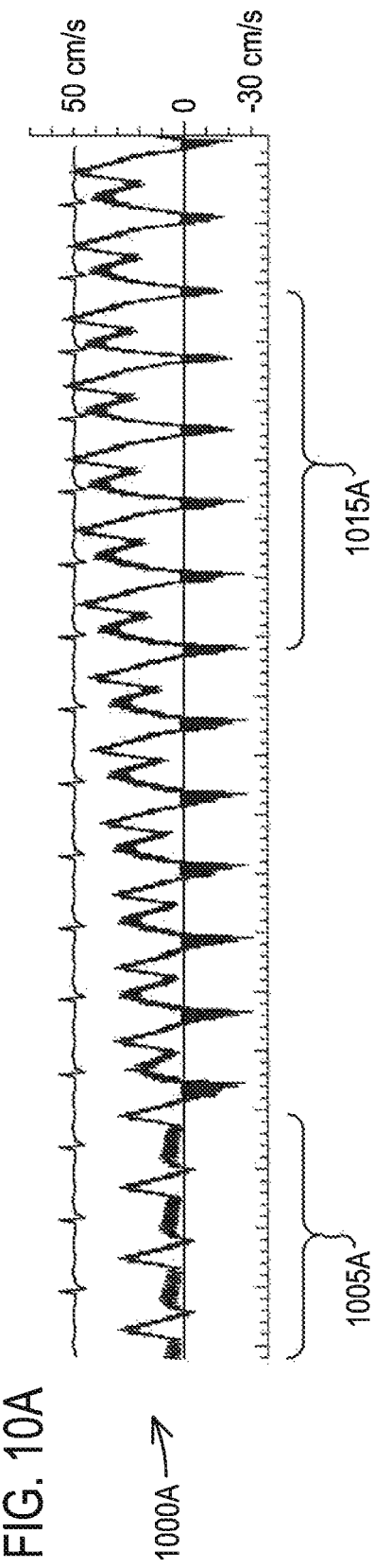
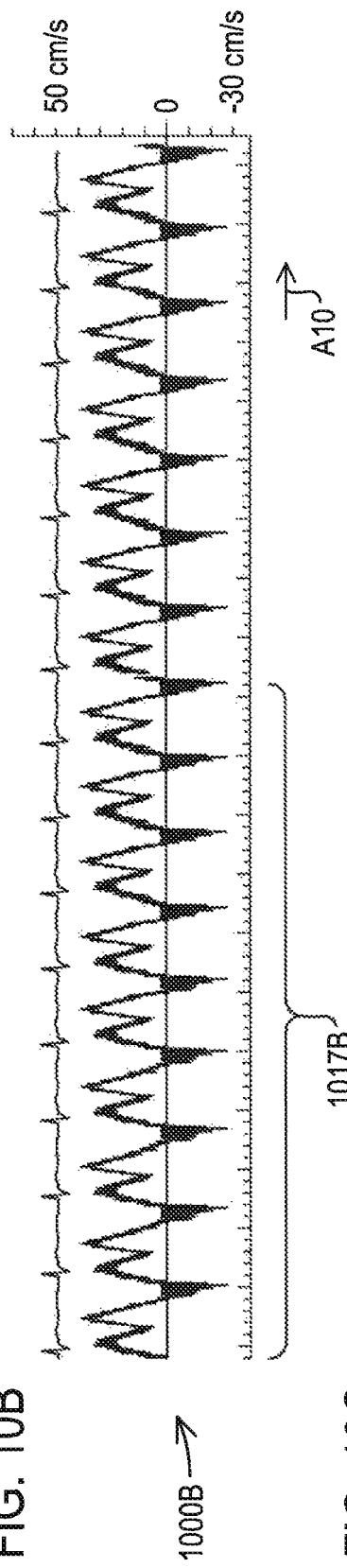
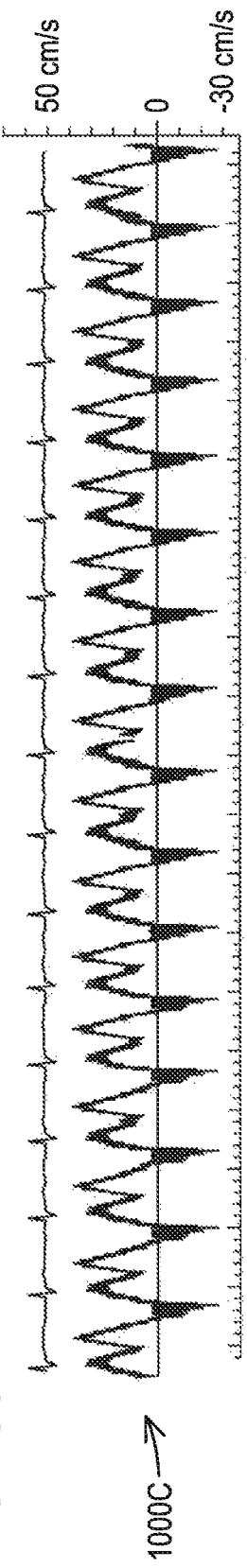
FIG. 10A
FIG. 10B
FIG. 10C

SYSTEM AND METHOD FOR SYNCHRONIZING EXTERNAL COMPRESSION OF A LIMB FOR INCREASED BLOOD

CROSS-REFERENCE TO RELATED APPLICATIONS

This application claims benefit of U.S. Provisional Application No. 62/142,931 filed Apr. 3, 2015, incorporated herein by reference as if set forth in full below.

BACKGROUND

Embodiments relate to devices, systems and methods of assisting in blood flow to the heart from a limb.

The vasculature in the body includes veins which have one-way valves to prevent a backflow of blood. In the lower extremities, extra work is required to move blood against gravity to the input side (right atrium) of the heart. The skeletal muscles assist the heart during perambulatory motion by compressing veins in the lower extremities, aiding in emptying the venous circulation and therefore provide assistance in returning blood back to the heart against gravity. The skeletal muscles of the calf or lower extremity muscle groups including, but not limited to, the major muscle groups such as the soleus muscle and gastrocnemius muscle, have been identified as supporting this function. The lower extremity muscle group's actions in facilitating the return of blood back to the heart are referred to as the skeletal muscle pump (human muscle pump) or as the second heart because these muscles provide assistive pumping of venous blood back to the heart from the periphery. The actions, namely, contraction of the muscles and resulting peristaltic blood flow in the lower extremities is generally known as the skeletal muscle pump, or the second heart effect. The skeletal muscle pump is essential for maintaining adequate venous and interstitial fluid flows in the dependent body.

During periods of inactivity or immobility, the continuous circulation of oxygenated blood throughout the body remains important for homeostatic function. In specific instances of inactivity, the increased circulation of oxygenated blood can aid in future periods of perambulatory motion and/or clinical treatment of a variety of diseases. This includes, but is not limited to, the removal of metabolic waste products from localized tissue regions, amelioration of the symptoms of muscle fatigue, improved muscle performance in subsequent bouts of exercise, and reducing the likelihood of thrombus formation. For clinical treatments, increased circulation can prevent/reduce the likelihood for thrombus formation, aid with wound healing, reduction of edema, and reduce the stress on the cardiovascular system.

SUMMARY

Embodiments related to devices, systems and methods of assisting blood flow to the heart from a limb. In an aspect, a device is provided comprising a wearable garment; and a compression apparatus embedded in the garment for applying an external compression according to a compression sequence to a muscle of a limb of a user based on real-time measurements regarding a cardiac cycle having a diastolic phase and systolic phase of the user and real-time measurements of muscle activity. The compression sequence is synchronized to commence when both the local blood flow at the limb is in the diastolic phase and the muscle is in a non-contracted state.

An aspect of the embodiments include a system comprising a wearable garment to be worn on a limb of a user; a cardiac cycle sensor to perform real-time measurements regarding a cardiac cycle having a diastolic phase and systolic phase of the user; a muscle activity sensor to perform real-time measurements of muscle contractions in the limb. The system includes a compression apparatus embedded in the garment for applying an external compression to the limb of the user. A processor is coupled to the compression apparatus to control the compression apparatus to apply pressure, according to a compression sequence, to a muscle of the limb based on the real-time measurements of the cardiac cycle of the user and the real-time measurements of the muscle activity. The compression sequence is synchronized to commence when both the local blood flow at the limb is in the diastolic phase and the muscle is in a non-contracted state.

An aspect of the embodiments includes a method comprising: sensing, by a cardiac cycle sensor, real-time measurements regarding a cardiac cycle having a diastolic phase and systolic phase of a user; sensing, by a muscle activity sensor, real-time measurements of muscle activity in a limb of the user; applying compression, by a compression apparatus, to a muscle in the limb of the user, and controlling the compression, by a processor coupled to the compression apparatus, according to a compression sequence, based on the real-time measurements of the cardiac cycle of the user and the real-time measurements of the muscle contractions wherein the compression sequence is synchronized to commence when both the local blood flow at the limb is in the diastolic phase and the muscle is in a non-contracted state.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 3E shows a second side of muscle compression system according to a second wrap configuration;

FIG. 3F shows a top view of the muscle compression system according to the wrap configuration;

FIG. 5 shows another flowchart of a method to compress a muscle of a limb according to an embodiment;

FIGS. 7A, 7B and 7C show graphs of Doppler ultrasound measurements of the blood flow in the popliteal artery without compression assistance, during unsynchronized compression assistance and during diastolic phase compression assistance, respectively;

FIGS. 10A, 10B and 10C show graphs of ultrasound measurements of popliteal arterial blood flow demonstrating the sustained impact of properly timed compression over 2-minute compression period, namely, at a first 10-second interval, a second 10-second interval and a last 10-second interval, respectively;

DETAILED DESCRIPTION

Figure 1A:
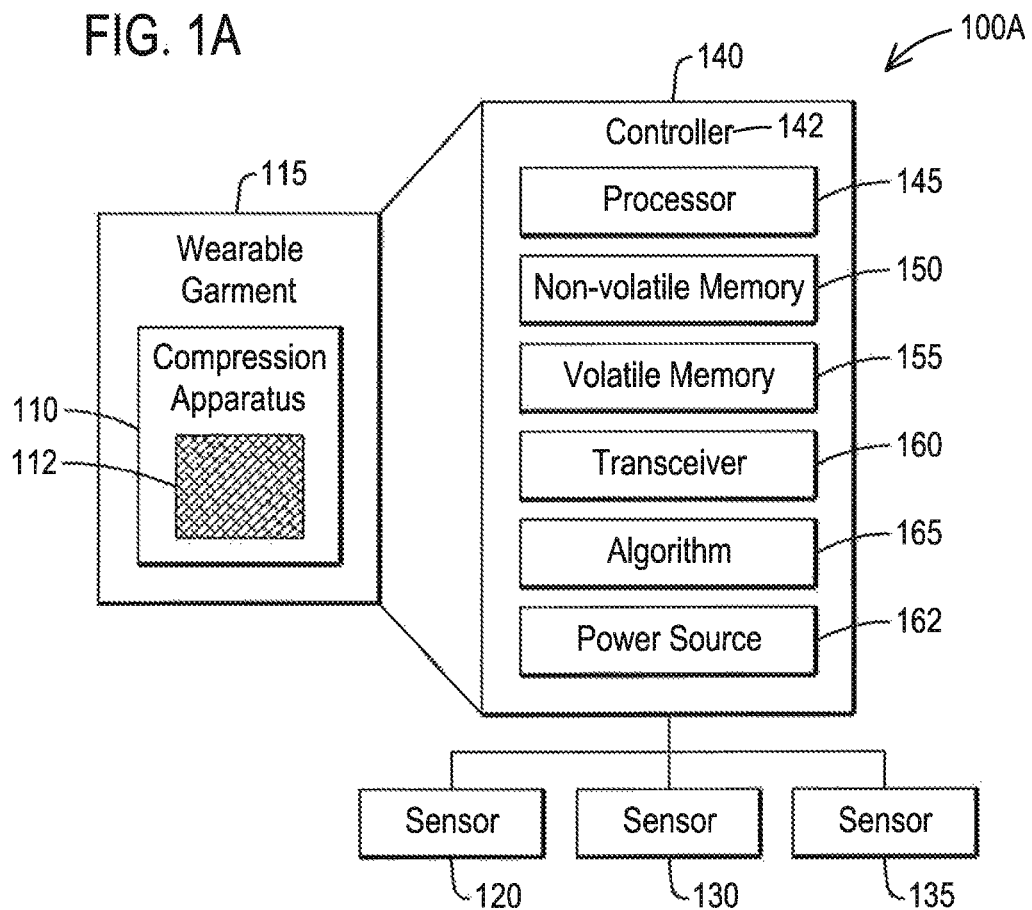
FIG. 1A shows a block diagram of a muscle compression system according to an embodiment.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "between 0 and 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4. In some instances, the range may have negative values Muscles require a continuous supply of oxygenated blood to properly function and ward off fatigue (remove metabolic waste). The ability of the body to perform perambulatory motion for an extended period of time is limited by various factors, some of which include genetics, physical fitness level and cardiovascular efficiency. A subject has an ability to increase oxygen introduced into the subject's body to a genetic maximum efficiency ($VO_{2MAX}$) through exercise and training. Once $VO_{2MAX}$ is reached, the subject usually seeks to maintain this peak efficiency for as long as possible while continuing perambulatory motion. In the presence of pathology, perambulatory motion can be made difficult by a reduction in the circulation of blood and reduced delivery of oxygenated blood.

During periods of inactivity or immobility, the continuous circulation of oxygenated blood throughout the body remains important for homeostatic function. In specific instances of inactivity, the increased circulation of oxygenated blood can aid in future periods of perambulatory motion and clinical treatment of a variety of diseases. This includes, but is not limited to, the removal of metabolic waste products from localized tissue regions, amelioration of the symptoms of muscle fatigue, improved muscle performance in subsequent bouts of exercise, and reducing the likelihood of thrombus formation. For clinical treatments, increased circulation can prevent/reduce the likelihood for thrombus formation, aid with wound healing, reduce edema, and reduce the stress on the cardiovascular system.

The apparatus, system and processes described herein provide assistance to the wearer by reducing the effort the heart must perform to maintain, supplement, or enhance cardiovascular performance to accomplish a task or work at hand.

The apparatus, system and processes described herein below provide assistance to the wearer by improving the local blood flow to the region to aid in recovery after surgery.

The apparatus, system and processes described herein may be particularly applicable to soldiers, athletes, and other active individuals who depend on good circulation to maintain cardiovascular performance sufficient to accomplish the task or work at hand. Thus, such individuals may benefit from being able to increase benefits achieved via the activation of the skeletal muscle pump (muscle contraction). During periods when the muscle pump is inactive, individuals benefit from being able to maintain or exceed the circulatory benefits present during periods of perambulatory motion.

FIG. 1A shows a block diagram of an embodiment of a system 100A. As illustrated, the system 100A may comprise a compression apparatus 110 that is provided to apply pressure to a limb of a user. A limb may be a leg, such as a lower leg (such as, without limitation, beneath a knee of the user). In other embodiments, the limb may be an arm. The compression apparatus 110 may be applied above the knee, as well.

The compression apparatus 110 may be a part of a wearable sleeve, sock or garment 115, which is configured to be worn, or fit around the limb. The compression apparatus 110 may comprise a smart material 112 such as, but not limited to, an electroactive polymer. In FIG. 1A, the smart material 112 is represented as a fabric. Thus, in a non-limiting example, the electroactive polymer may be integrated directly into a wearable garment 115. The smart material 112 may include an artificial muscle wherein an artificial muscle includes materials which may contract in response to a stimulus such as electric current or voltage and expand in response to another stimulus or the removal of the stimulus. The terms smart material, electroactive polymer and artificial muscle may be used interchangeably.

The compression apparatus 110 may be able to constrict, or apply pressure, upon receiving an electrical signal to cause the compression apparatus 110 to either constrict/contract or expand. A non-limiting example of an amount of compression may be approximately 20-160 mmHg wherein "approximately" is used to mean plus or minus 10.

The system 100A may include a control system 140 having a controller 142, as disclosed in more detail herein, may be set to a maximum applied pressure within this range.

As explained in further detail below, timing and degree of compression applied by the compression apparatus 110 may be dictated by signal feedback from at least one of physiological sensors and pressure sensors, respectively. The use of smart materials 112 allows for actuation of the compression apparatus 110 to occur fast enough to apply compression within a fraction of one cardiac cycle and repeat compression during each cardiac cycle or a subset of heartbeats, in accordance with the details of compression described herein. The application of compression which occurs within one diastolic phase of a cardiac cycle may be referred to as the "compression sequence." The compression sequence will be described in more detail in relation to FIG. 3A.

The system 100A may include a plurality of sensors 120, 130 and 135. Sensor 120 hereinafter being referred to as a first sensor 120. Sensor 130 hereinafter being referred to as a second sensor 130. Sensor 135 hereinafter being referred to as a third sensor 135.

The first sensor 120 may be located on the limb. A non-limiting example of where the first sensor 120 may be located is in between the limb and the compression apparatus 110. A non-limiting example of the first sensor 120 may be a surface electromyography ("EMG") sensor. The first sensor 120 is also sometimes referred to as the muscle activity sensor.

The first sensor 120 may determine, in real-time, a contraction state, or activity, of a muscle in the limb. With the first sensor 120, muscle activity may be determined by monitoring and recording electrical activity associated with muscle contractions. As a non-limiting example, the first sensor 120 may be used to monitor electrical activity in a limb muscle, such as the calf muscles, specifically the gastrocnemius and soleus muscles. In an embodiment, the limb muscle may be in the thigh, the upper arm or the forearm, for example.

The first sensor 120 may be wired or wireless and integrated into the wearable compression apparatus 110. Direct measurement of the electrical activity of the muscle allows for clear determination of muscle contraction patterns, which may be used to determine a window of time when compression would be most beneficial. As a non-limiting example, during muscle contraction, intramuscular pressure is very high and external compression would not be capable of supplementing the actions of the contracted muscle. In turn, external compression would be of little benefit while the calf muscle is contracted. The inventors have determined that external compression would be most beneficial when the muscle is relaxed, or in a non-contracted state, and intramuscular pressure is low.

In addition to analysis of muscle contraction, direct monitoring of muscle electrical signals facilitates the analysis of gait information.

In an embodiment, the first sensor 120 may indirectly identify muscle activity, such as via an accelerometer to determine limb motion and time compression based upon the readings from the accelerometer. The first sensor 120 may include a plurality of sensors or sensor suite wherein the collective data of the suite determines motion or non-motion of a limb to which compression is to be performed. The first sensor 120 may include a force sensor, near infrared spectroscopy (NIRS) sensor, or electromyography (EMG) sensor.

The second sensor 130 may be provided to measure, in real-time, the systolic and diastolic time delay, cycle or rhythm, wherein the measurement may be taken at the limb. The second sensor is sometimes referred to as the cardiac cycle sensor. The second sensor 130 may be a non-invasive peripheral blood flow sensor such as, but not limited to, a pulse photoplethysmograph ("PPG") or near infrared spectroscopy sensor (NIRS). The second sensor 130 may be remote from the garment as will be described later. Peripheral blood flow patterns of the user may be used to set and modify the compression timing of the compression apparatus 110 and makes the compression apparatus 110 customizable to the anatomy and physiology (such, as, but not limited to, vascular system) of the user. More specifically, this measurement may provide for directly measuring arrival of the arterial pulse wave at the limb, which is delayed relative to the timing of the cardiac contraction given by measurements of heart rate from an electrocardiogram (ECG). Such delay may be due to height, physical condition, or heretical features of the user. Thus, the pulse wave delay relative to the timing of the cardiac contraction varies between individuals and further emphasizes the importance of measuring local blood flow at the limb.

In an embodiment, the diastolic phase is a local diastolic phase in one cardiac cycle according to a limb to which compression is to be applied.

The third sensor 135 may be provided to measure compression to ensure that an identified amount of pressure is actually being applied. The third sensor 135 may sometimes be referred to as the pressure sensor. The first sensor 120 and the second sensor 130 may be taking real-time, continuous readings of activity associated with the limb wherein the third sensor 135 may be taking real-time, continuous readings either when compression is being applied or even when compressive phases are not being applied. With respect to the plurality of sensors 120, 130 and 135, when readings are made may be defined as information associated with each sensor may be collected for other reasons, such as, but not limited to, other medical reasons.

The controller 142 may be in communication with the first sensor 120 and the second sensor 130 to cause the compression apparatus 110 to apply a pressure (compression) to the limb when both the diastolic phase of the local blood flow in the limb takes place and the muscle is in a non-contracted state. The controller 142 may comprise a processor 145 such as, but not limited to, a microprocessor. Other parts of the controller 142 may be, but is not limited to, volatile memory 150, non-volatile memory 155, a transceiver 160, and algorithms 165, or computer program instructions, disclosed later herein. The controller 142 or control system 140 may include a power source 162. In some embodiments, the power may be derived externally. For example, power may be derived externally from a shoe as described in U.S. patent application Ser. No. 13/954,364 entitled "SYSTEM AND METHOD FOR SUPPLEMENTING CIRCULATION IN A BODY" filed Jul. 30, 2013, and assigned to Lockheed Martin Corporation, which is incorporated herein by reference as if set forth in full. In other embodiments, the power source 162 may include a battery source which may be rechargeable.

The controller 142 may also determine an amount of pressure to apply with the compression apparatus 110 to the limb. Thus, the controller 142 may cause the compression apparatus 110 to vary an amount of pressure applied to the limb based on a rate of blood flow desired in the limb. The third sensor 135 provides feedback to the controller 142 to vary the compression of the compression apparatus 110 until it reaches the right pressure.

In some embodiments, the algorithm 165 utilized in the controller 142 may be used to identify a swing phase of walking by the user, when the calf muscle is not contracted, based on the electrical activity and the muscle activity information will be used to determine the actions of the compression system 100A. The algorithm 165 operated by the control system 140 may be used to identify the local diastolic phase of the local blood flow pattern. Though a single algorithm is disclosed, the functions described may be performed by a plurality of algorithms.

The processor 145 may include any type of stationary computing device or a mobile computing device. The processor 145 may include one or more processors. Depending on the exact configuration and type of computing device, system memory may be volatile (such as RAM), non-volatile (such as read only memory (ROM), flash memory, and the like) or some combination of the two. System memory may store an operating system, one or more applications, and may include program data for performing the process of methods 400 and 500, described in detail below. The control system 140 may carry out one or more blocks of methods 400 and 500. The control system 140 may also have additional features or functionality. For example, control system 140 may also include additional data storage devices (removable and/or non-removable) such as, for example, magnetic disks, optical disks, or tape. Computer storage media may include volatile and non-volatile, non-transitory, removable and non-removable media implemented in any method or technology for storage of data, such as computer readable instructions, data structures, program modules or other data. System memory, removable storage and non-removable storage are all examples of computer storage media. Computer storage media includes, but is not limited to, RAM, ROM, Electrically Erasable Read-Only Memory (EEPROM), flash memory or other memory technology, compact-disc-read-only memory (CD-ROM), digital versatile disks (DVD) or other optical storage, magnetic cassettes, magnetic tape, magnetic disk storage or other magnetic storage devices, or any other physical medium which can be used to store the desired data and which can be accessed by a processor. Any such computer storage media may be part of the control system 140.

The control system 140 may also include or have interfaces for input device(s) (not shown) such as a keyboard, mouse, pen, voice input device, touch input device, etc. In an embodiment, the control system 140 may store collected data from sensors and provide a cardiac analysis report or performance analysis, such as related to any of the graphs described herein.

The control system 140 may include a peripheral bus for connecting to peripherals. The control system 140 may contain communication connection(s) or transceiver 160 that allow the system 140 to communicate with other computing devices, such as over a network or a wireless network. By way of example, and not limitation, communication connection(s) may include wired media such as a wired network or direct-wired connection, and wireless media such as acoustic, radio frequency (RF), infrared and other wireless media. The control system 140 may include a network interface card to connect (wired or wireless) to a network.

Computer program code for carrying out operations described above may be written in a variety of programming languages, including but not limited to a high-level programming language, such as C or C++, for development convenience. In addition, computer program code for carrying out operations of embodiments described herein may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed Digital Signal Processor (DSP) or microcontroller. A code in which a program of the embodiments is described can be included as a firmware in a RAM, a ROM and a flash memory. Otherwise, the code can be stored in a tangible computer-readable storage medium such as a magnetic tape, a flexible disc, a hard disc, a compact disc, a photo-magnetic disc, a digital versatile disc (DVD).

In the embodiment of FIG. 1A, the compression apparatus 110 may include an electromagnet device in lieu of smart material 112, where the electromagnet device being configured to cause compression in response to an electrical stimulus. In an embodiment, the compression apparatus 110 may include a pneumatic device or mechanical device to perform the compression. In such configurations, the compression apparatus 110 would receive a source of pneumatic fluid (air or liquid) under the control of control system 140. Furthermore, the system 100 may include a pneumatic fluid source (not shown).

In an embodiment, the controller 142 may vary the voltage or current supplied to the artificial muscle, smart material or electromagnet. In another embodiment, the controller 142 may vary a working or pneumatic fluid channeled to bladders of the compression apparatus 110.

Hybrid configurations may be implemented. A non-limiting example, a hybrid configuration may include structural instabilities to exploit rapid transition between two states, as with snap-actuators. Alternatively, combined electromagnetic/hydraulic systems can be implemented including, but not limited to, magneto-reactive fluids or solenoid pistons.

Figure 1B:
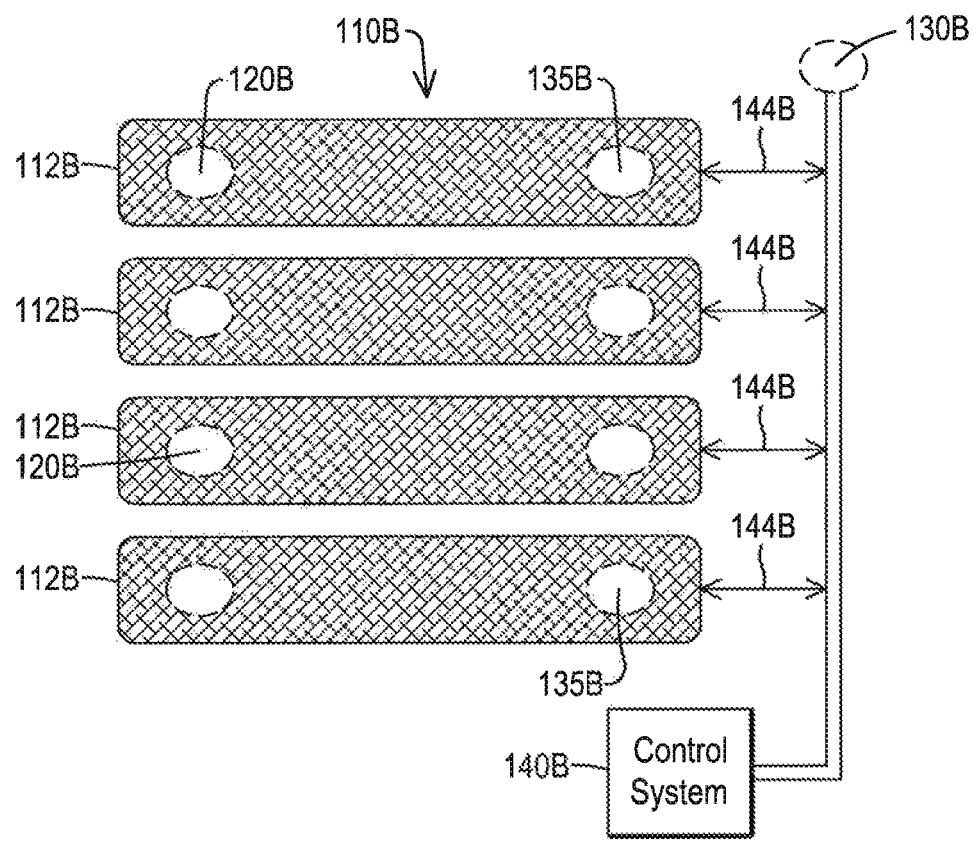
FIG. 1B shows a schematic diagram of muscle compression system according to an embodiment.

FIG. 1B shows a schematic diagram of a muscle compression system according to an embodiment. Each segment 112B of the compression apparatus 110B may comprise connections to a data, power and/or compression timing bus 144B from the control system 140B. Each segment 112B of the compression apparatus 110B connects to the data, power and compression bus 144B. The bus 144B may include a single line or multiple lines to permit communications between each segment (denoted at 110B) and the control system 140B. Communications may include sensor data transferred from sensors 120B and 135B from the segment to the control system 140B. Communications may include the transfer of a current or voltage such as an electrical stimulus to activate the segment such as the artificial muscle, represented as cross-hatched to denote a fabric, threads or an electroactive polymer. The communication protocol used may provide rapid access to each segment on a one-by-one basis by the control system 140B. The bus 144B may provide power to the plurality of sensors 120B, 130B and 135B. Each segment may sometimes be referred to as a compression cuff. The segment may completely surround the limb muscle or partially surround the limb muscle.

The plurality of sensors 120B, 130B and 135B are represented as dashed line circles. The sensors 120B and 135B may be integrated in an active layer within the segments, as will be described in more detail. While the sensors 120B and 135B are represented as dashed lines, in each segment, one or more of the sensors may be omitted. For example, not all segments may require a muscle activity sensor. Therefore, the layers of the segments may vary.

The sensor 130B is represented separate from the segments of the compression apparatus 110B. However, the sensor 130B in an embodiment is integrated into the garment 115 (FIG. 1A) at a location which allows the cardiac cycle to be sensed.

Figure 2A:
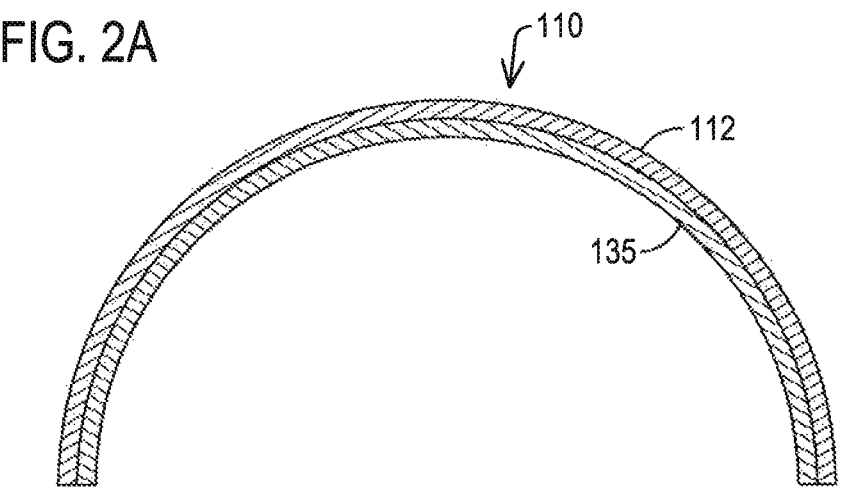
FIG. 2A shows a partial view of a compression segment according to an embodiment.

FIG. 2A shows a partial view of a compression segment of the compression apparatus 110 according to an embodiment. The compression apparatus 110 may comprise multiple layers of materials such as, but not limited to, two layers of materials. As illustrated a layer closest to the limb may be or comprise the sensor 135 which is provided to measure an actual pressure being applied. An outer, or second layer, may be or comprise the electroactive polymer, or smart material 112.

Figure 2B:
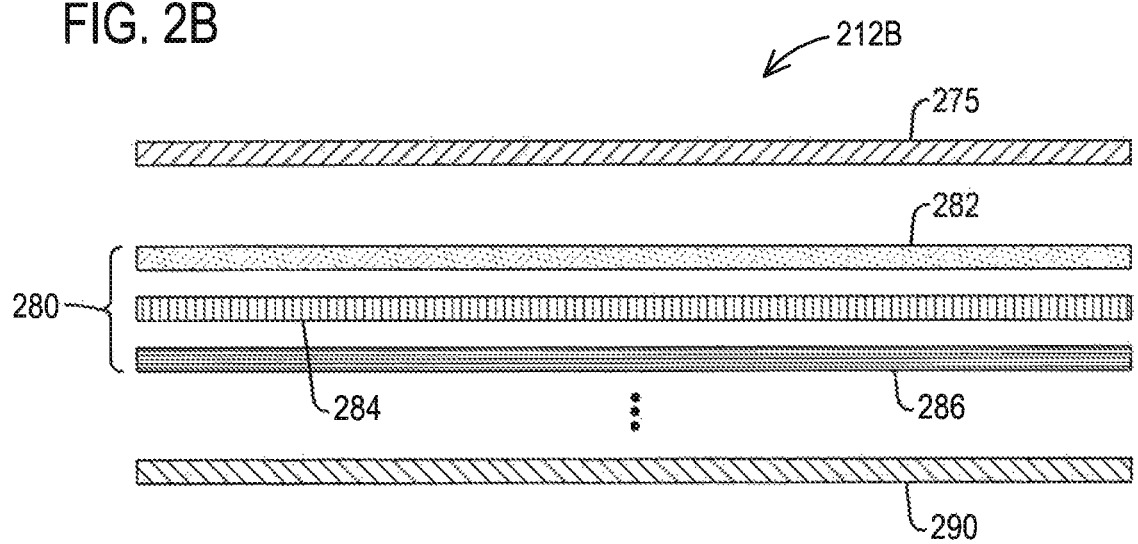
FIG. 2B shows multiple layers of a compression segment according to an embodiment.

FIG. 2B shows multiple layers of a compression segment 212B according to an embodiment. Each of segments 212B may comprise a data, power and/or compression connection to the control system 140B. Each segment 212B connects to a data, power and compression bus. The segment 212B is a modular segment. As shown in FIG. 2B, the segment 112 (FIG. 1A) includes two layers.

The modular segment 212B may have a plurality of layers that can be varied based on the application needs. The segment 212B includes a plurality of active layers 280. The active layers include layers 282, 284 and 286. There can be more or less layers used as dictated by the application. Additionally, some layers as shown can be implemented as a single "physical" layer or with portals through layers connecting element layers together. For example, layer 282 may be a muscle activity sensor layer which may serve as the muscle activity sensor. Layer 284 may be a pressure sensor layer which may serve as the pressure sensor. Layer 286 may be a compression layer which may include an artificial muscle, for example.

In the illustration, layers 275 and 290 are shown sandwiching the active layers 280 and may be part of the garment 115 (FIG. 1A). The layer 275 may be an inside or interior layer wherein the inside or interior layer being in direct contact with the skin of the wearer. Layer 290 may be an exterior layer.

In an embodiment, the pressure sensor layer (i.e., layer 284) and muscle activity sensor layer (i.e., layer 282) might be integrated into a single physical layer or single physical unit. As an additional example, the muscle activity sensor layer (i.e., layer 282) and the inside or interior layer 275 might be integrated so that elements of the sensor pass through the layer 275 to make skin contact. The active layers 280 may be enclosed by layers 275 and 290 which protect the wearer and the active layers such as from sweat from the wearer and moisture in the environment, for example. One implementation of the layers 275 and 290 integrate all necessary active layers. In some embodiments, the compression layer 286 may move separately from any of the other layers wherein the compression layer 286 provides a compressive force to the limb it is wrapped around.

Figure 3A:
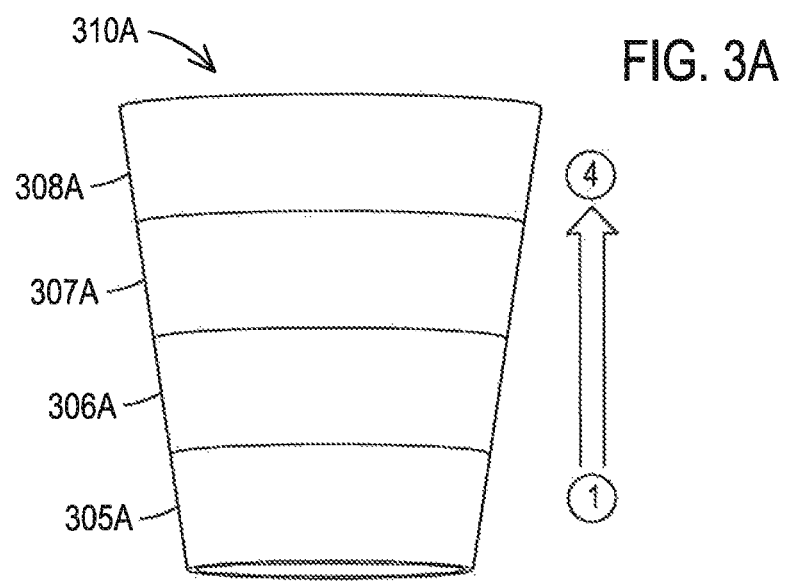
FIG. 3A shows a compression apparatus of a muscle compression system according to a sleeve configuration.

FIG. 3A shows a compression apparatus 310A of a muscle compression system according to a sleeve configuration. As shown, the compression apparatus 310A may have a plurality of compression segments 305A, 306A, 307A, and 308A. Instead of each segment 305A, 306A, 307A, and 308A compressing at the same time, compression takes place according to a compression sequence. The compression sequence may begin at the (first) segment 305A furthest from a heart of the user and conclude at the (last) segment 308A closest to the heart of the user during the local diastolic phase of the blood flow. Compression on any intermediate segments 306A and 307A follows in a similar sequence between the first segment 305A and the last segment 308A. While the embodiment illustrates four segments, the apparatus 310A may have more or less segments. During compression, the segment constricts to exert a force of pressure on the limb or limb muscle. Compression is released or terminated after the compression sequence, upon detection of the end of the diastolic phase of the cardiac cycle.

The third sensor 135 may be provided for each segment 305A, 306A, 307A, and 308A so that pressure may be measured for each compression to ensure that compression reaches a desired pressure for each segment.

The sleeve configuration generally surrounds the limb and maintains its position on the limb during a non-compression state. The sleeve is generally continuous with the circumference varied to accommodate the anatomical profile of a portion of the limb whether the calf, thigh, upper arm or forearm. In an embodiment, the compression segments may be integrated into a sock. In a sock configuration, the compression segments may be located in the portion which fits around the calf and above the ankle.

Figure 3B:
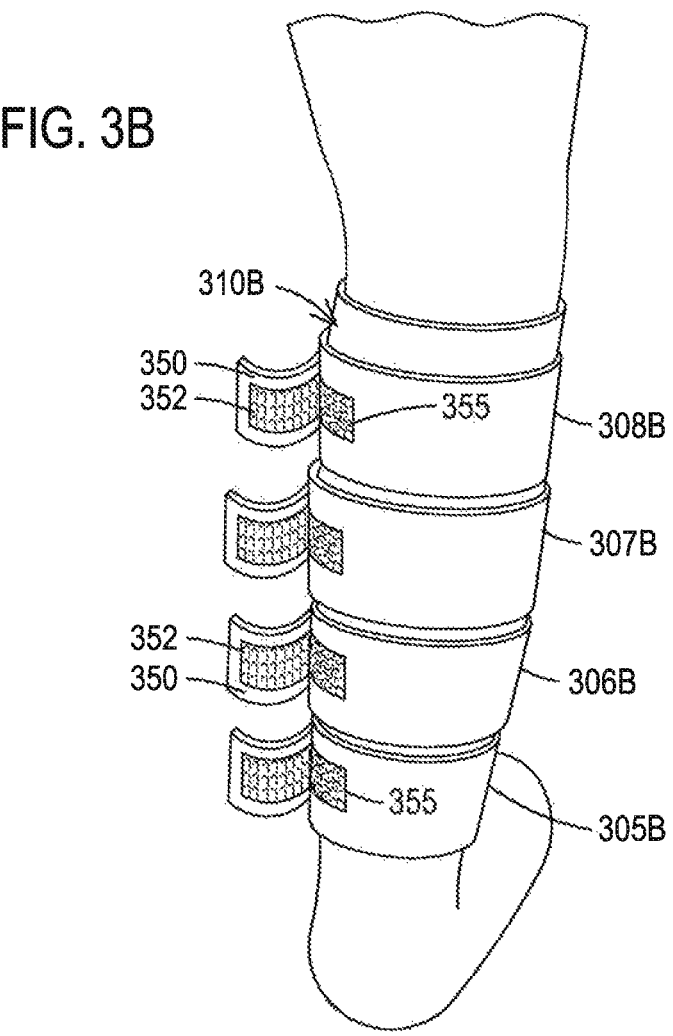
FIG. 3B shows a muscle compression system attached to a user's limb.

FIG. 3B shows another embodiment of a backside of the compression apparatus 310B. As illustrated in FIG. 3B, the segments may not form a continuous compression apparatus 310B as disclosed in FIG. 3A. Instead, each segment 305B, 306B, 307B and 308B may be an individual strip with tabs 350 which can be sized to fit a user using hook and loop fastening assemblies 352 and 355. The strip can be tightened around the limb for a snug fit. The strip may be layered as described in FIG. 2B.

Though both FIG. 3A and FIG. 3B show multiple segments where a milking pattern is utilized (as represented by the arrow in between 1 and 4), these embodiments are not meant to be limiting. In another non-limiting example, a different compression sequence may be utilized. For example, the compression sequence may include activating for compression segments 305A and 307A, together or in series; or segments 306A and 308A together or in series. The compression sequence may repeat at least once or until the diastolic phase is complete in the current cardiac cycle or muscle activity is sensed. The compression sequence may be varied based on the expected duration of the diastolic phase wherein the diastolic phase may vary such as the result of the intensity of activity of the wearer. Thus, the compression sequence may be synchronized to the diastolic phase.

In yet another non-limiting example, the compression apparatus 310A or 310B may not have multiple compression segments, but may have a single compression segment. The single compression segment may exert a force of pressure for a duration of the diastolic phase. The single compression segment may exert a force of pressure which is applied and then relaxed repeatedly for the duration of the diastolic phase or until muscle activity is sensed.

In the embodiment of FIG. 3B, the second sensor 130 (FIG. 1A) may be attached to the limb from or through the apparatus.

In a non-limiting example, the amount of compression for each segment may vary based on blood flow measured with the second sensor 130. More specifically, each segment may be compressed based on local arterial blood flow and local muscle activation. Thus, compression per segment may be provided only when the monitored readings identify when compression is most beneficial. Though compression is to be performed during the diastolic phase, compressive subsets may be performed during this phase. As a non-limiting example, a rate of compression may be at a level to provide for two complete compressive cycles (compression sequence) of the segments to occur. In another non-limiting example, only a smaller subset of segments may be utilized.

Monitoring the amount of pressure applied may be done with the controller 142 employing a real time data processing to monitor physiological parameters such as, but not limited to, heartbeats and mechanical parameters such as, but not limited to, applied pressure, in order to control when and how much pressure is applied to the limb. Real time data processing may involve continuous monitoring of the applied pressure and comparison to a pre-set maximum applied pressure. This ensures that the desired operating pressure is achieved for each compression and compression is ceased once this threshold is met.

Thus, as illustrated above, an apparatus may be provided for applying external compression to the limb of the user based on real-time readings regarding a cardiac cycle of the user measured at the limb and muscle contractions measured at the limb. Compression is applied when both the local blood flow is in a diastolic phase, as measured on the limb, and the muscle is in a non-contracted state. The smart material such as, but not limited to, an electroactive polymer is a part of the apparatus and which provides for the actual compressive effect. In an embodiment, the artificial muscle is at least partially located around the limb, namely, at a backside and along sides of the limb. When the limb is a leg, the artificial muscle wraps around the gastrocnemius and soleus muscles located on the backside of the leg. More specifically, with respect to the leg, circumferential pressure may be preferred.

Figure 3C:
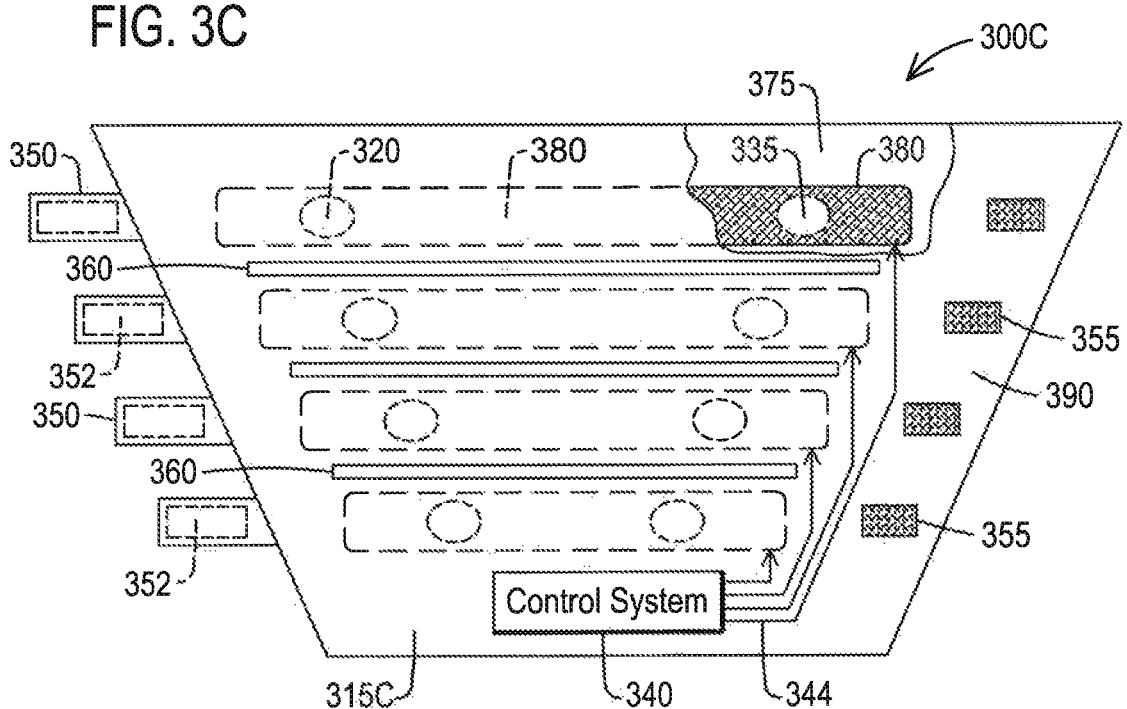
FIG. 3C shows a first side of muscle compression system according to a first wrap configuration.

FIG. 3C shows a first side of muscle compression system 300C according to a first wrap configuration. As a wrap, the garment 315C may be secured to a limb using hook-and-loop fastening straps 350 with hook and loop fasteners 352 and 355. The hook and loop fasteners 352 and 355 may be substituted with other fasteners, such as without limitation, zippers, adhesives, tapes, external flexible bandages, etc.

The muscle compression system 300C includes a plurality of active layers 380 embedded or sandwiched between layers 373 and 390 with layer 390 partially removed to show the underlying layers of the active layer 380 and the layer 375. Between the segments, gaps 360 are provided. The gap 360 may represent the absence of material. The active layers 380 may include sensors 320 or 335 denoted by the dashed circle. The sensor may be integrated into the layers or a separate element. As also described previously, one or more sensors may be omitted for a particular segment.

The control system 340 communicates with the active layers 380 and/or sensors 320 and 335. In this embodiment, the sensor 330 is omitted, but may be included. For example, in some embodiments, the cardiac cycle sensor 330 may be remote from the garment 315C so that the cardiac cycle may be sensed elsewhere on the wearer's body. Hence, the remote cardiac cycle sensor would communicate with the control system 340 to provide the cardiac cycle timing so that the compression sequence can be derived.

The number of segments may vary. The length of the segment is shorter than the width of the garment. However, the length of the segment should allow a compression effect on the limb or limb muscle to be realized when worn. The segment is represented as an elongated rectangular member. The width of the garment corresponds to the dimension which wraps around the circumference of the limb.

The width of the wrap may also enable the system to be sized for different wearer body types as well as applicability to different limbs (i.e. calf, thigh, forearm, and upper arm).

Figure 3D:
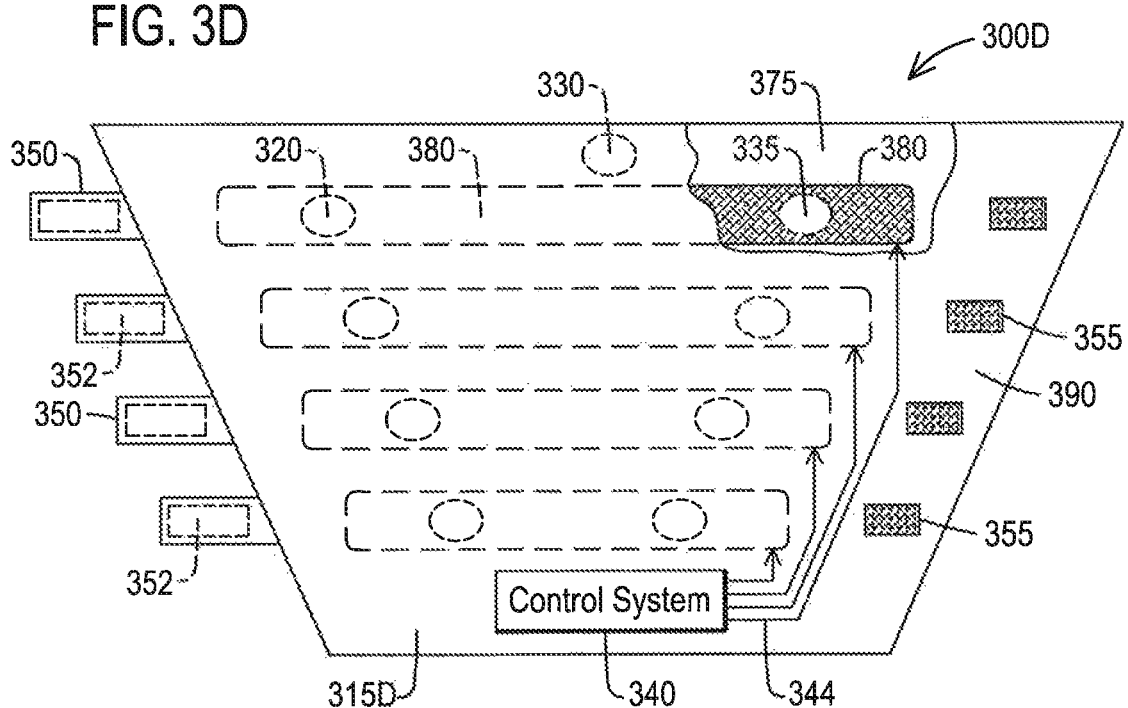
FIG. 3D shows a first side of a muscle compression system according to a second wrap configuration.

FIG. 3D shows a first side of a muscle compression system 300D according to a second wrap configuration. In this configuration, the gaps 360 have been omitted and the cardiac cycle sensor 330 is shown embedded in the garment between the layer 375 and layer 390. The sensor 330 is shown at the top of the garment 315D.

FIG. 3E shows a second side of muscle compression system 300E according to a second wrap configuration with a portion of layer 375 removed exposing a portion of a segment with active layers 380 and layer 390.

FIG. 3F shows a top view of the muscle compression system 300F according to a wrap configuration. The compression system 300F is in a wrapped or installed state around a limb. The modular segments take up a part or all of the circumference of the garment wrap 315F. The wrap itself may not completely surround a limb, but rather have the fasteners to complete the loop around the limb. The hook-and-loop fastening straps 350 may go completely around the garment 315F or may be only a small size to close the loop, as shown. The modular segments are surrounded by the layers 390 and 375 and the system 300F is held in place by hook-and-loop fastening straps 350 (or other methods as described previously). The external layer 390 is inelastic and does not stretch. When the compression layer in the active layer 380 is activated, the external layer 390 directs the compression inwards towards the limb being compressed, in the direction of the arrows shown.

Figure 4:
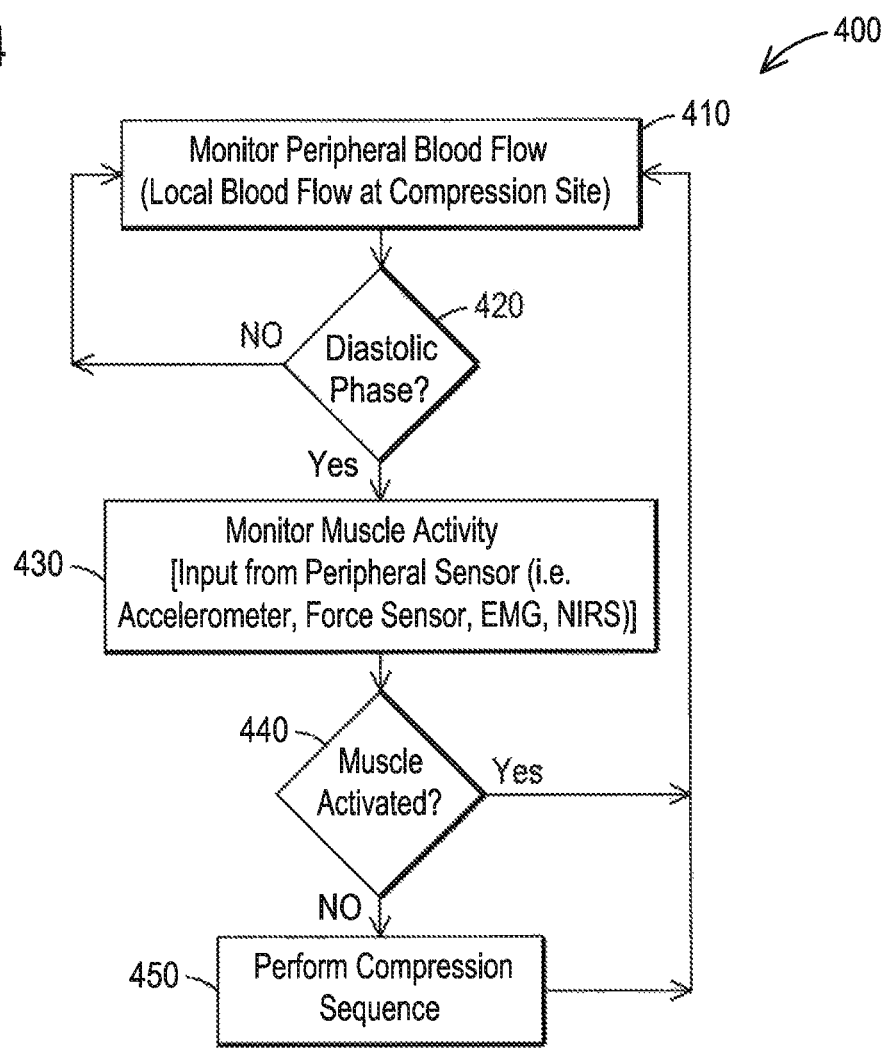
FIG. 4 shows a flowchart of a method to compress a muscle of a limb according to an embodiment.

FIG. 4 shows a flowchart of a method 400 to compress a muscle of a limb according to an embodiment. The methods and processes shown herein are for illustrative purposes and represented in a series of blocks. The blocks may be performed sequentially in the order shown or in a different order. One or more of the blocks may be performed contemporaneously. Furthermore, one or more of the blocks may be added or omitted.

In some embodiment, the system 100A is worn during motion of the user such as during work or sports activities. In some embodiment, system 100A may be used such as while a user is sleeping. However, while sleeping, the user may get up or may move their legs. Thus, as will be apparent from the description herein, the compression is not applied during muscle movement, activity or contraction. In some embodiments, the compression is only applied for the fraction of time in the cardiac cycle that relates to the diastolic phase or period.

As illustrated, the method 400 comprises monitoring, or measuring, peripheral blood flow, namely, blood flow, at block 410. In an embodiment, the blood flow may be measured locally at the limb. In an embodiment, the blood flow may be measured at the heart. Based on the monitoring, at block 410, a determination is made when the cardiac cycle is either in a diastolic phase or at the end of a systolic phase, at block 420. If the blood flow is measured locally, the local diastolic phase (or end of a systolic phase) is used to directly synchronize the compression timing. If the blood flow is measured at the heart of the wearer/user such as by a remote cardiac cycle sensor, a delay is used to synchronize timing of the compression to the local diastolic phase realized at the limb. If the diastolic phase is not detected at block 420, the method loops back to block 410.

If the diastolic phase is detected based on the determination at block 420, monitoring of muscle activity of the limb occurs, at block 430. A determination is made if the muscle is activated, or in a contracted state, at block 440. If the muscle is not contracted, or in a non-activated (or relaxed) state, compression occurs, at block 450. If in a contracted state or the muscle is detected as being activated, no compression occurs and the method loops back to block 410. In other words, the compression timing synchronization to a local diastolic phase is essentially aborted/terminated. However, cardiac cycle monitoring/sensing and muscle activity may be performed essentially continuously. Block 450 loops back to block 410.

In operation, the compression sequence may be repeated such that multiple compression sequences are used in a single diastolic phase or the compression sequence may be one sequence to terminate at or near the end of the diastolic phase.

The method may be supplemented with additional blocks related to the sensing/monitoring of the pressure being applied by the compression cuff wherein the compression effect caused by the compression apparatus may be varied based on the pressure sensing readings.

FIG. 5 shows another flowchart of a method. As illustrated the method 500 provides for monitoring, in real-time, peripheral blood flow at a limb of a user with at least a first sensor attached at the limb, at block 510. The method 500 also comprises determining, in real-time with at least the first sensor, when the heart of the user is in a diastolic phase based on the monitored blood flow at the limb, at block 520. If the peripheral blood flow is determined to be in a diastolic phase, the method 500 further comprises determining, in real-time, whether a muscle in the limb is in a non-contracted state with at least a second sensor, at block 530. If the muscle is in the non-contracted state, the method further comprises applying pressure to the muscle with a compression apparatus as initiated by a controller, at block 540.

The method may further comprise measuring pressure applied by the compression apparatus to ensure that a correct amount of pressure is applied during compression, at block 550. The method 500 may further comprise analyzing when the muscle is in the non-contracted state to further determine when to apply pressure to the muscle, at block 560. As can be appreciated one or more of the blocks may be performed contemporaneously with other blocks. Furthermore, the order may be modified.

Applying pressure (compression) to the muscle with the compression apparatus may further comprise, during the diastolic phase, applying pressure in a sequence with the compression apparatus having a plurality of sections individually compressible which apply pressure in a sequence where a first section furthest from the heart is contracted, or compressed, first and a last section that is closest to the heart is contracted, or compressed, last.

Thus, in operation, each individual compression may be based on information garnered from sensors measuring local arterial blood flow and muscle activation. This information may be used as input to a real time control system, as part of a controller, to quickly react to changes in physiological behavior and determine when compression should be applied. Further, the timing of compression based on local arterial blood flow allows for independent timing for each limb based on current local conditions. The timing of compression may be relative to each heartbeat, but can also be customized to a subset of heartbeats such as, but not limited to, compressions every other heartbeat. The limb will be actively compressed only after the completion of the systolic phase of the localized blood flow. That is, compression will occur during the diastolic phases of the local blood flow. No external compression would be applied during the systolic portion.

When actual compression occurs is important based on physiological and energy usage reasons. Regarding the physiology based reasoning, timing will prevent a potential increase in cardiac afterload, which is the pressure the left ventricle must overcome to eject blood from the heart, and disruption of blood flow into the limb. Peripheral blood flow information will be used in conjunction with information garnered from muscle activity sensors as input into the timing control for the compression system. It is noted that diastolic phases of the local blood flow may not necessarily align with the periods of calf or limb muscle relaxation. In turn, it may be advantageous to apply compression only when muscle relaxation occurs simultaneously with the diastolic phase of the local blood flow. This triggering based on this timing cycle would require the monitoring of both the flow cycle and limb muscle activity to determine the initiation of compression. As for the energy usage reason, by applying compression only when it will have the most physiological benefit, energy used by the compression system can be reduced. As a non-limiting example, compression during muscle activity does not have physiological benefit, so energy is conserved by delaying compression until muscle contraction has ended.

Figure 6A:
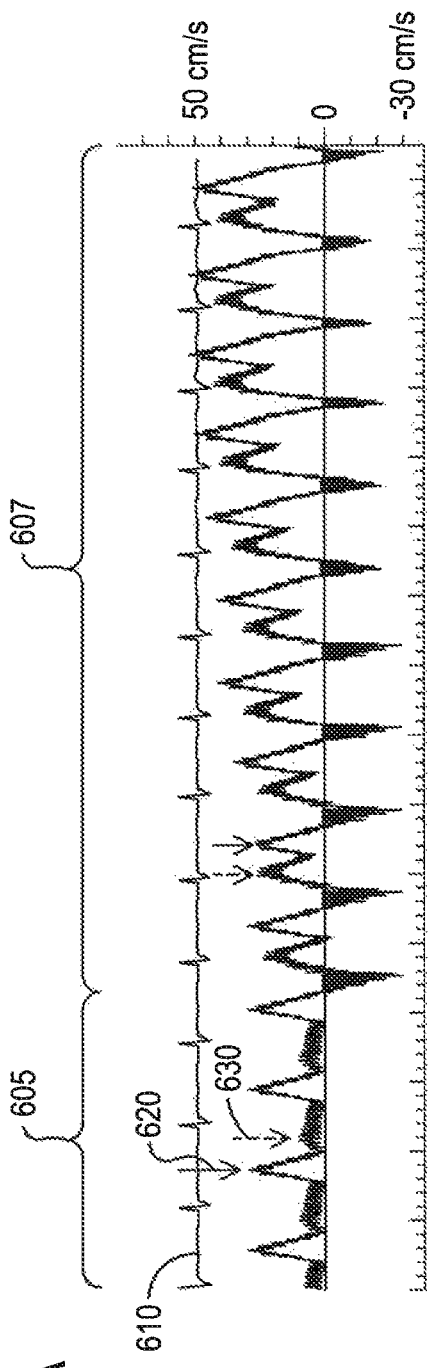
FIGS. 6A and 6B show results realized by utilizing an embodiment of the system or method disclosed herein.
Figure 6B:
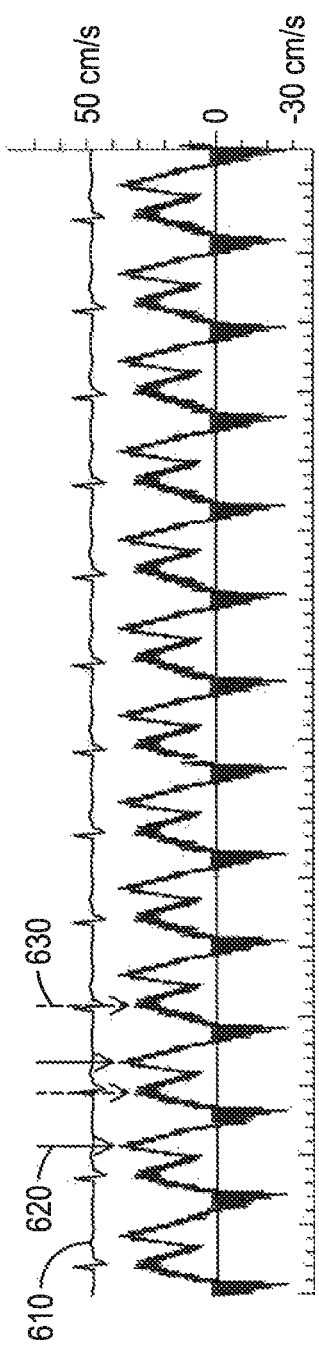

FIGS. 6A and 6B show results realized by utilizing an embodiment of the systems or methods disclosed herein. The results are illustrated as ultrasound waves measured at the leg in the popliteal artery. As shown in FIG. 6A, when no compression is applied, at 605, a systolic peak, denoted by arrow 620, is higher (more blood is flowing) than at the diastolic peak (less blood is flowing as the heart is relaxed), denoted as arrow 630. When compression is applied, at 607 during the diastolic phase of the cardiac cycle, blood flow is then increased during the diastolic phase. FIG. 6B illustrates the effects of the increased blood flow continues even after 2 minutes of compression, during the diastolic phase. Arrows 630 are represented in dashed lines while arrows 620 are solid.

As is also illustrated in FIGS. 6A and 6B, a top line 610 shows the heart rate measured at the heart, namely, not on the limb. The measurements below the top line 610 are taken at the limb. As explained above, the measurements at these different locations indicate a time shift between the contraction of the heart and arrival of the systolic pulse wave locally at the limb, which will be unique person to person. This further illustrates why measuring local blood flow at the limb is preferred.

FIGS. 7A, 7B and 7C show graphs 700A, 700B and 700C of Doppler ultrasound measurements of the blood flow in the popliteal artery without compression assistance, during unsynchronized compression assistance and during diastolic phase compression assistance, respectively. The benefits of compressing during the diastolic portion of the local cardiac cycle as outlined in this patent is demonstrated via the examination of changes in blood delivery to the calf region. While the graphs are directed to the leg/limb and calf region, the muscle compression system may be used on the arm muscles, such as in the upper arm or forearm.

In FIG. 7A, a Doppler ultrasound measurement of the blood flow in the popliteal artery is shown, which is the main conduit artery supplying blood flow to the calf region, without the application of compression. The solid arrows 720A indicate the systolic peaks, indicative of blood flow into the lower limb that is driven by the contraction of the heart. The dashed arrows 730A indicate the diastolic phase in which blood flow has slowed into the leg.

During this phase, the contraction of the heart has ceased and ventricular refilling is occurring (blood is returning to the heart)

FIG. 7B shows the augmentation of the popliteal artery blood flow with the application of compression to the calf region. The compression is applied during every heartbeat, but timed predominately during the systolic phase (outside of the local diastole phases). The solid arrows 720B indicate a reduction in blood flow into the leg with each contraction of the heart. This has two main detrimental effects on the cardiac and lower limb muscle function. The first effect is the blunted systolic peak indicates a potential increase in cardiac afterload, which is the pressure the left ventricle must overcome to eject blood from the heart. Over time, this can put stress on the heart as it pumps harder to overcome the resistance to flow imparted by improper compression timing. The second effect is that the reduction of blood flow into the lower limb reduces the availability of oxygenated blood to the leg muscles.

Many devices on the market now apply compression at a time interval irrespective of the physiological signals, such as the cardiac cycle, which can reduce circulation and in some cases increase the likelihood of blood pooling and clotting in the lower limbs.

FIG. 7C shows the augmentation of the popliteal artery blood flow due to the application of compression based on the timing algorithm outlined in this patent. Specifically, the compression is applied during the local diastolic phases. The solid arrows 720C indicate the higher systolic peak and the dashed arrow 730C indicate the significantly increased diastolic flow with our compression technique. Overall, the oxygenated blood delivered to the calf muscle is increased within a cardiac cycle increasing the efficiency of the heart and reducing heart rate as a result of increased cardiac output with each contraction. The increased circulation in the leg helps to remove metabolic waste products that can cause muscle fatigue and soreness.

The benefits of compression such as during exercise can be evident from the description and graphs below. The exercise conducted included application of pressure on a foot pedal.

Figure 8A:
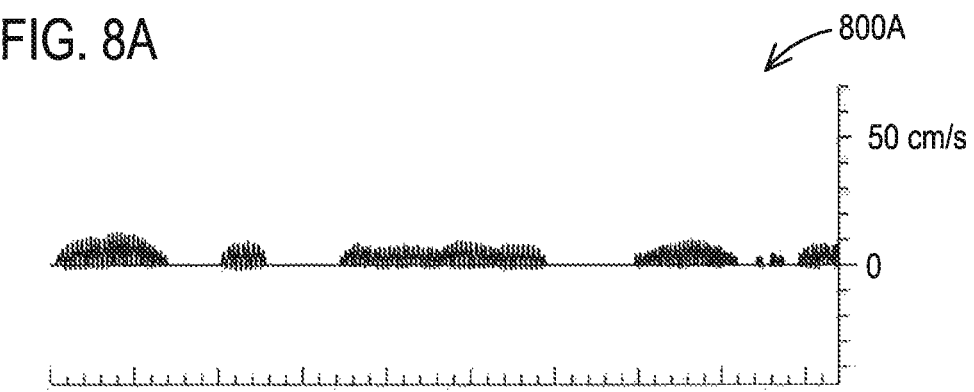
FIGS. 8A, 8B and 8C show graphs of venous flow at rest, during exercise and based on compression assistance, respectively.
Figure 8B:
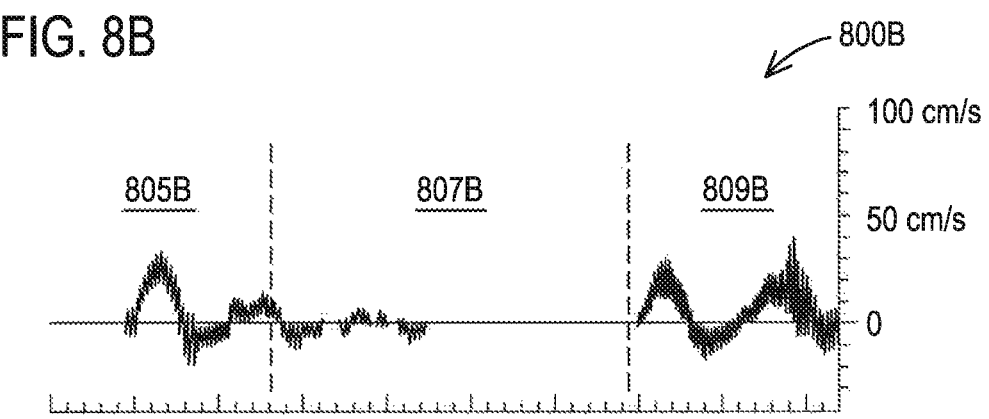
Figure 8C:
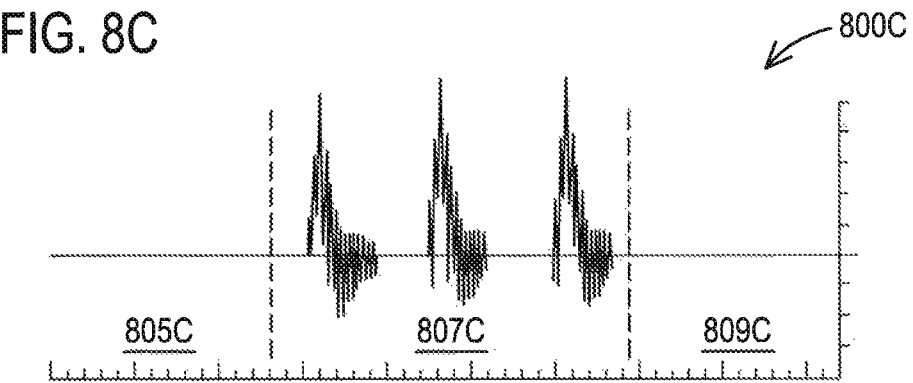

FIGS. 8A, 8B and 8C show graphs 800A, 800B and 800C of venous flow at rest, during exercise and based on compression assistance, respectively. The timing of compression with physiological signals and feedback regarding muscle activity has been shown to be beneficial. The venous blood flow (blood flow back to the heart) velocity profile showed large changes with exercise and with the application of compression. In the graphs of FIGS. 8B and 8C, the contraction (active) states 805B, 805C, 809B and 809C of the muscle and the relaxed (inactive) states 807B and 807C of the muscle are marked or demarcated by the vertical dashed lines.

Figure 9A:
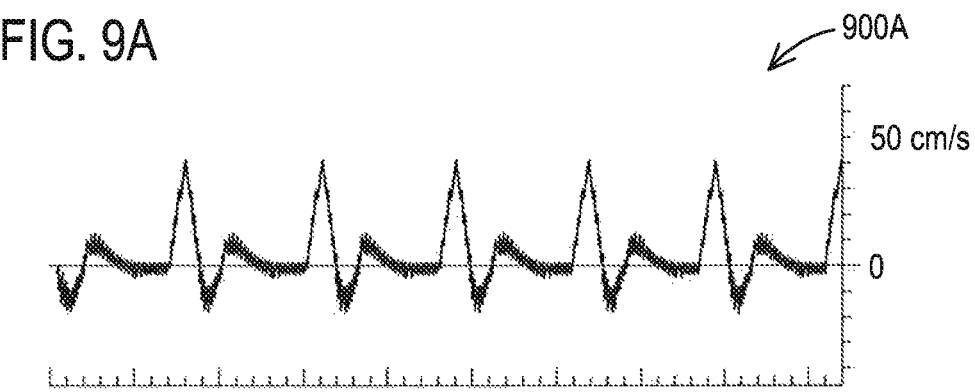
FIGS. 9A, 9B and 9C show graphs of arterial flow at rest, during exercise and based on compression assistance, respectively.
Figure 9B:
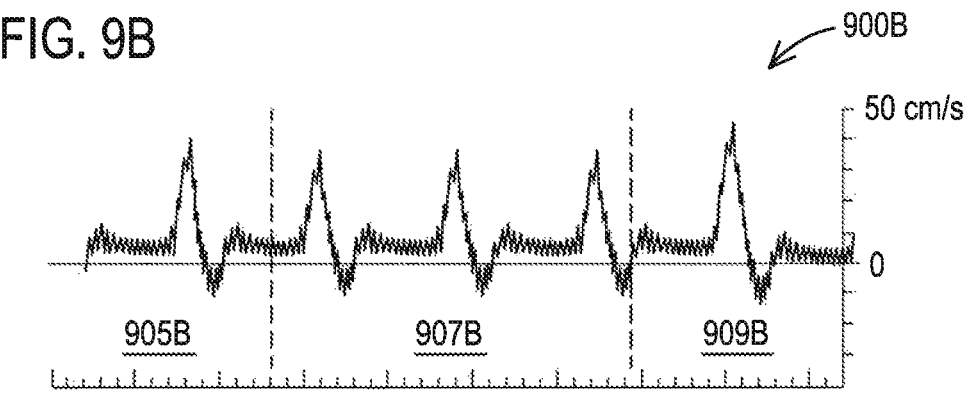
Figure 9C:
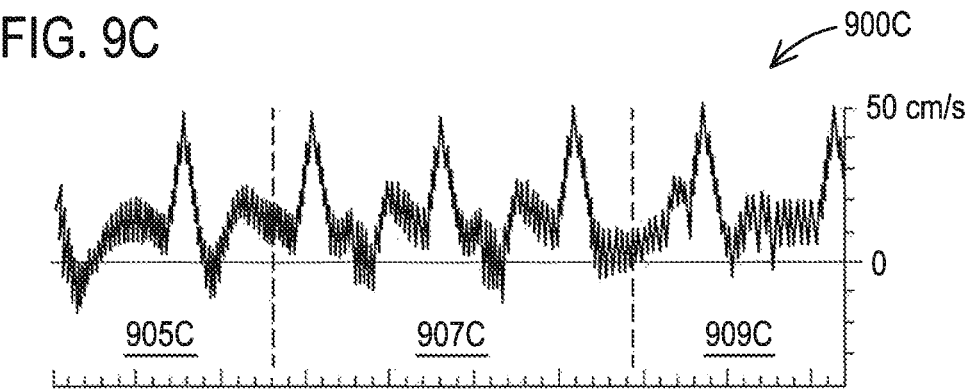

FIGS. 9A, 9B and 9C show graphs of arterial flow 900A, 900B and 900C at rest, during exercise and based on compression assistance, respectively. In the graphs of FIGS. 9B and 9C, the contraction (active) states 905B, 905C, 909B and 909C of the muscle and the relaxed (inactive) states 907B and 907C of the muscle are marked or demarcated by the vertical dashed lines.

With the depression of a weighted foot pedal, the muscle pump was activated resulting in increased popliteal venous blood flow (FIG. 8B) as would normally happen during walking. During the relaxation phase 807B when the pedal is not pressed, venous flow decreases and blood pools in the leg/limb. In contrast, when active compression was applied, timed to the periods in which the muscle pump is not active and during the diastolic phase of the cardiac cycle, venous flow was increased during the resting phase of exercise with each compression 807C (FIG. 8C). Again, work is reduced for the heart due to more blood returned and expelled for each beat and active compression aids in venous return when the muscle pump is "off." On the arterial side (FIG. 9C), circulation is increased during the relaxation phase active state of exercise with the proper timing of compression (the periods in which the muscle pump is not active and during the diastolic phase of the cardiac cycle) 907C.

FIGS. 10A, 10B and 10C show graphs 1000A, 1000B and 1000C of ultrasound measurements of popliteal arterial blood flow demonstrating the sustained impact of properly timed compression over a 2-minute compression period, namely, at a first 10-second interval, a second 10-second interval and a last 10-second interval, respectively. At 1005A, a baseline is shown in the ultrasound measurements. At 1015A, an increase in the peak velocity is shown.

In FIG. 10B, a decrease in peak velocity is shown in 1017B with a steady state represented at arrow A 10.

Figure 11:
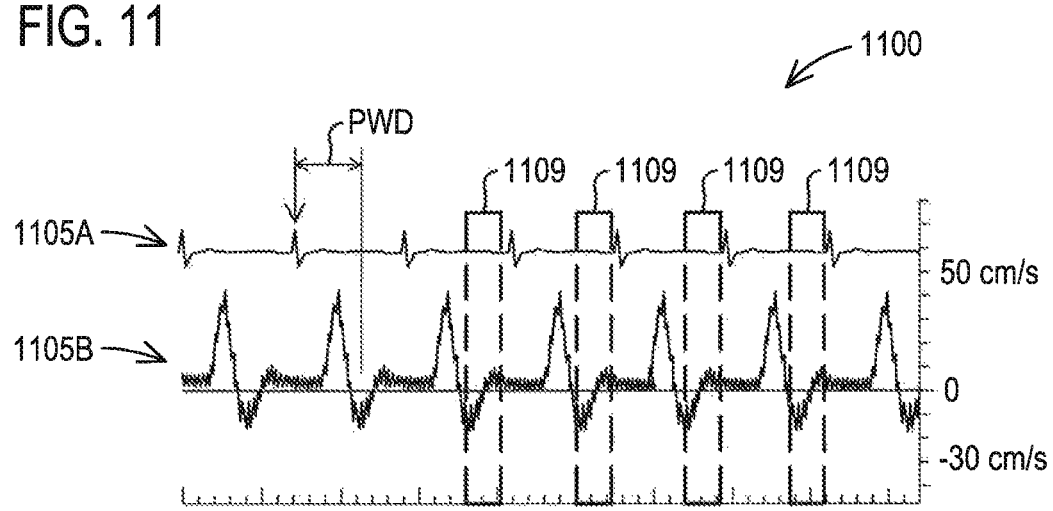
FIG. 11 shows a graph of an electrocardiogram (ECG) signal correlated to flow of a popliteal artery velocity with timing of compression.

FIG. 11 shows a graph 1100 of an electrocardiogram (ECG) signal 1105A correlated to flow of a popliteal artery velocity 1105B with timing of compression represented as lines 1109. The graph 1100 represents the timing of compression 1109 relative to the ECG signal 1105A measured at the heart and the local peripheral blood flow 1105B measured using Doppler ultrasound at the compression site on the leg. The compression occurs during the local diastolic phase of the local blood flow avoiding the systolic phases. The pulse wave delay period PWD is noted on the graph to represent the difference in local and remote diastolic phase commencements.

Figure 12:
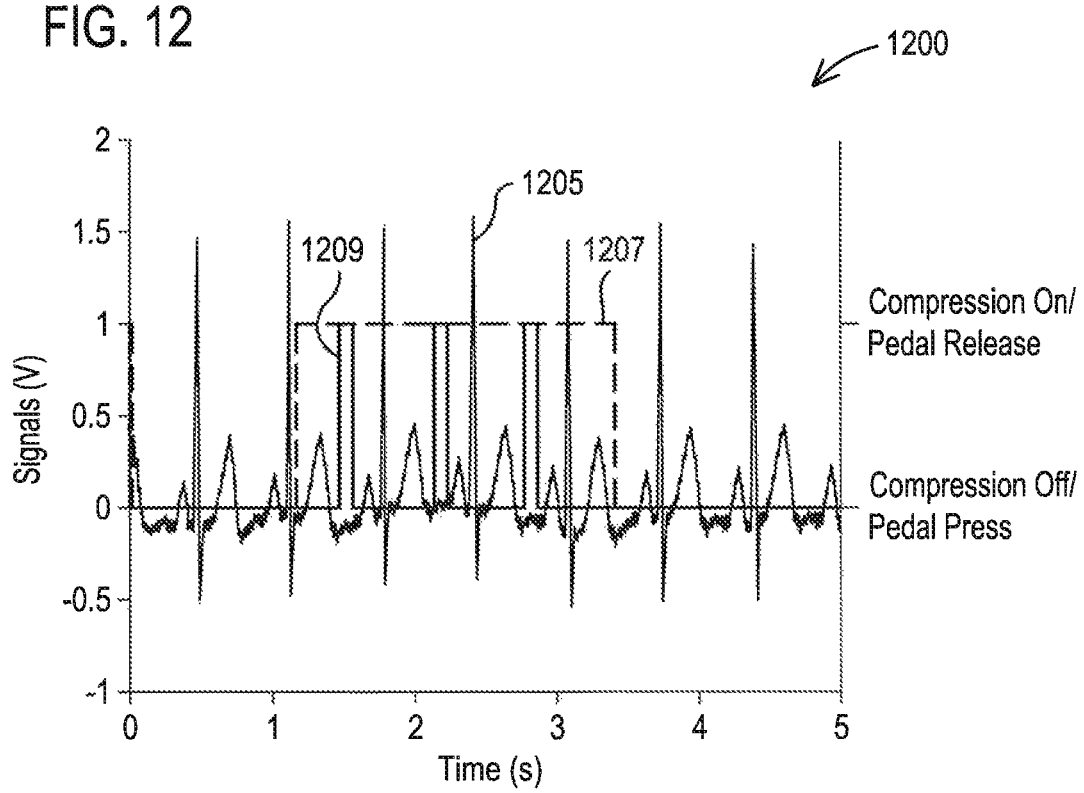
FIG. 12 shows a graph of timing of compression during diastolic phase and when the muscle is in an inactive state.

FIG. 12 shows a graph 1200 of timing of compression during diastolic phase and when the muscle is in an inactive state of a wearer. The graph will vary based on muscle activity assuming that the diastolic phase essentially repeats itself after the systolic phase according to the same time interval. The graph 1200 represents the timing of compression (lines), denoted as numeral 1209, during light exercise (pressing a foot pedal) represented in a dashed line, denoted at 1207. The graph 1200 indicates the application of compression 1209 only during the period when the pedal is not pressed (muscle is not activated/being used). The timing is shown in reference to the ECG signal 1205A measured at the heart indicating compression occurs late in the cardiac diastolic phase to account for the pulse wave time delay, denoted as PWD in FIG. 11, to the compression site on the leg/limb. In an embodiment, the compression cycle would be synchronized according to the local diastolic phase according to the local timing realized in the limb. If the diastolic cycle measurements are taken remote from the limb to be compressed, the PWD pulse wave time delay PWD should be compensated for in order to synchronize the measurements of the cardiac diastolic cycle to the local diastolic cycle.

Figure 13:
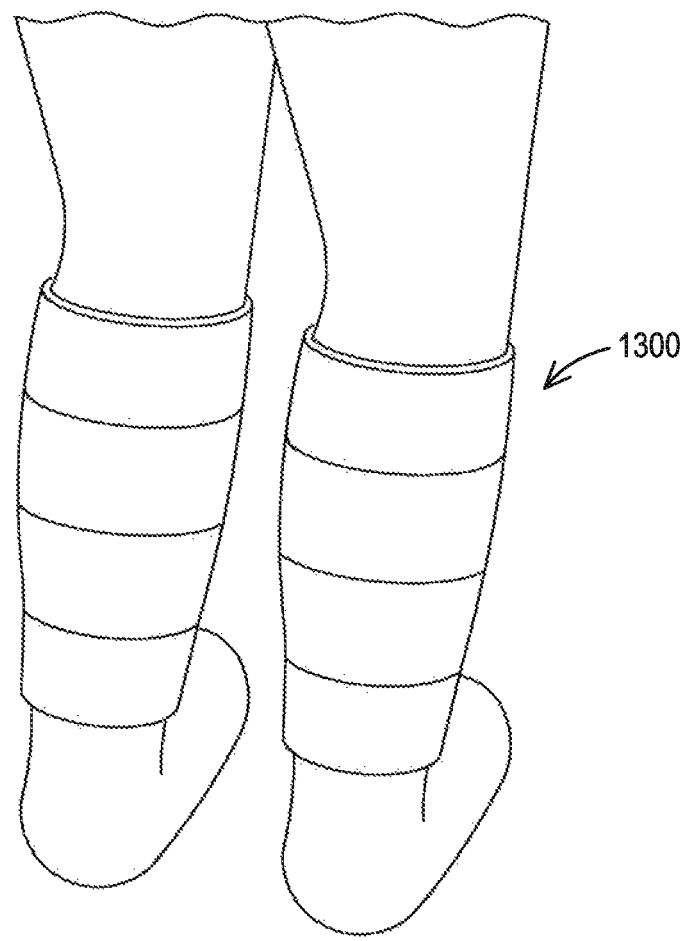
FIG. 13 shows a wearer using a pair of compression systems on legs according to an embodiment.

FIG. 13 shows a wearer using a pair of compression systems 1300 on legs according to an embodiment. In some embodiment, the wearer may want to use only one system 100A on one limb such as for recovery after surgery or for other applications. In some embodiments, the wearer may want to use two systems 100A of FIG. 1A, represented as system 1300, or other configurations described herein, on each leg. The wearer may use two or more systems 100A according to their needs on their limbs. In some pairs of systems 100A, one or more components of the control system on one limb may be eliminated.

Figure 14:
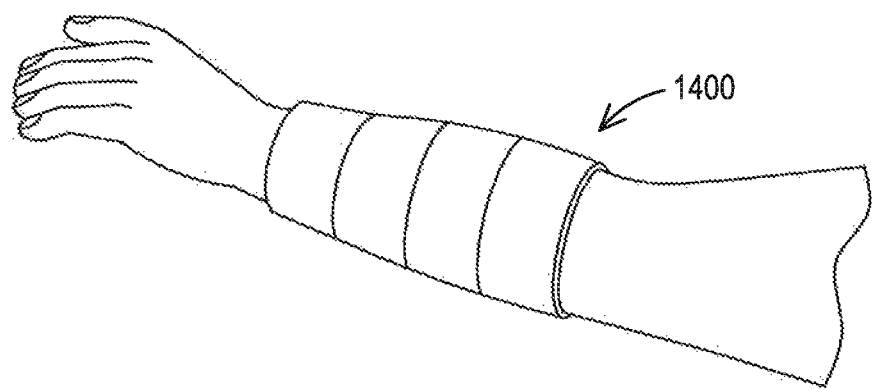
FIG. 14 shows a wearer using a muscle compression system on an arm according to an embodiment.

FIG. 14 shows a wearer using a muscle compression system 1400 on an arm according to an embodiment. The system 1400 is installed below the elbow. Nonetheless, the system 1400 may be worn above the elbow on the upper arm.

From a military, athletic, and physical laborer perspective, increased endurance, reduced fatigue and faster recovery times after physical activity may be realized. Those who sit for extended periods of time, such as, but not limited to, unmanned aerial vehicles ("UAV") pilots, extreme video garners who sit for extended durations, etc., may benefit from reduced blood pooling in their lower extremities. Air travelers may also benefit from a reduced risk of deep vein thrombosis ("DVT"). Airlines could supply embodiments disclosed herein to all passengers as they board an aircraft. The rhythmic compression helps blood continue circulating in the lower extremities and should reduce the risk of DVT. Embodiments may also be used by individuals in space to reduce loss of muscle mass when remaining in outer space for an extended period of time.

The "step-by-step process" for performing the claimed functions herein is a specific algorithm, and may be shown as a mathematical formula, in the text of the specification as prose, and/or in a flow chart. The instructions of the software program create a special purpose machine for carrying out the particular algorithm. Thus, in any means-plus-function claim herein in which the disclosed structure is a computer, or microprocessor, programmed to carry out an algorithm, the disclosed structure is not the general purpose computer, but rather the special purpose computer programmed to perform the disclosed algorithm.

A general purpose computer, or microprocessor, may be programmed to carry out the algorithm/steps for creating a new machine. The general purpose computer becomes a special purpose computer once it is programmed to perform particular functions pursuant to instructions from program software of the embodiments described herein. The instructions of the software program that carry out the algorithm/steps electrically change the general purpose computer by creating electrical paths within the device. These electrical paths create a special purpose machine for carrying out the particular algorithm/steps.

In particular, unless specifically stated otherwise as apparent from the discussion, it is appreciated that throughout the description, discussions utilizing terms such as "processing" or "computing" or "calculating" or "determining" or "displaying" or the like, refer to the action and processes of a control system, or similar electronic computing device, that manipulates and transforms data represented as physical (electronic) quantities within the computer system's registers and memories into other data similarly represented as physical quantities within the computer system memories or registers or other such data storage, transmission or display devices.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another.

Unless otherwise defined, all terms (including technical and scientific terms) used herein have the same meaning as commonly understood by one of ordinary skill in the art to which embodiments belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Therefore, the breadth and scope of the subject matter provided herein should not be limited by any of the above explicitly described embodiments. Rather, the scope of the embodiments should be defined in accordance with the following claims and their equivalents.

We claim:

1. A device comprising:
   a wearable garment;
   a compression apparatus embedded in the garment for applying an external compression to a limb of a user; and
   at least one of a processor or a controller configured to control the compression apparatus to apply the external compression, according to a compression sequence, to a muscle of the limb of the user based on real-time measurements regarding a cardiac cycle having a diastolic phase and systolic phase of the user and real-time measurements of muscle activity wherein the compression sequence is synchronized to commence when both a local blood flow at the limb is in the diastolic phase and the muscle is in a non-contracted state.

2. The device as set forth in claim 1, wherein the compression apparatus comprising a pressure sensor to sense an amount of pressure applied during compression.

3. The device as set forth in claim 1, wherein:
   the wearable garment comprises a wearable sleeve that fits around the limb; and
   the compression apparatus comprises a plurality of compression segments, each compression segment comprising an artificial muscle integrated in the wearable sleeve which in response to an electrical stimulus causes a compression state or an expansion state.

4. The device set forth in claim 3, wherein the compression sequence activates the plurality of compression segments beginning at a first compression segment of the plurality of compression segments being furthest from the heart of the user and concludes with a last compression segment of the plurality of compression segments corresponding to a location on the limb closest to the heart of the user, during the diastolic phase of the local blood flow.

5. The device set forth in claim 3, further comprising a plurality of sensors, the plurality of sensors comprising:
   a cardiac cycle sensor to perform the real-time measurements regarding the cardiac cycle having the diastolic phase and systolic phase of the user directly at the limb; and
   a muscle activity sensor to perform the real-time measurements of muscle contractions.

6. The device set forth in claim 5, further comprising a pressure sensor to sense an amount of pressure exerted by each compression segment of the plurality of compression segments of the compression apparatus.

7. The device set forth in claim 6, wherein the at least one of a processor or a controller is configured to determine the commencement of the compression sequence; and each compression segment comprising:
   a plurality of active layers in electrical communication with the at least one of a processor or a controller, the plurality of active layers being the pressure sensor, the artificial muscle and the muscle activity sensor.

8. A system comprising:
   a wearable garment to be worn on a limb of a user;
   a cardiac cycle sensor to perform real-time measurements regarding a cardiac cycle having a diastolic phase and systolic phase of the user;
   a muscle activity sensor to perform real-time measurements of muscle contractions on the limb;
   a compression apparatus embedded in the garment for applying an external compression to the limb of the user; and
   at least one of a processor or a controller coupled to the compression apparatus configured to control the compression apparatus to apply pressure, according to a compression sequence, to a muscle of the limb based on the real-time measurements of the cardiac cycle of the user and the real-time measurements of the muscle contractions wherein the compression sequence is synchronized to commence when both a local blood flow at the limb is in the diastolic phase and the muscle is in a non-contracted state.

9. The system set forth in claim 8, wherein the compression apparatus comprises a pressure sensor to sense an amount of pressure applied during compression.

10. The system set forth in claim 8, wherein:
    the wearable garment comprises a wearable sleeve that fits around the limb; and
    the compression apparatus comprises a plurality of compression segments, each compression segment comprising an artificial muscle integrated in the wearable sleeve which in response to an electrical stimulus causes a compression state or an expansion state.

11. The system set forth in claim 10, wherein the compression sequence activates the plurality of compression segments beginning at a first compression segment of the plurality of compression segments being furthest from the heart of the user and concludes with a last compression segment of the plurality of compression segments corresponding to a location on the limb closest to the heart of the user, during the diastolic phase of the local blood flow.

12. The system set forth in claim 10, wherein the cardiac cycle sensor being integrated in the wearable garment and in communication with the at least one of a processor or a controller.

13. The system set forth in claim 11, each compression segment comprising:
    a plurality of active layers being in electrical communication with the at least one of a processor or a controller, the plurality of active layers being a pressure sensor, the artificial muscle and the muscle activity sensor.

14. The system set forth in claim 8, further comprising:
    a second wearable garment to be worn on a second limb of the user;
    a second cardiac cycle sensor to perform real-time measurements regarding a cardiac cycle having a diastolic phase and systolic phase of the user in the second limb;
    a second muscle activity sensor to perform real-time measurements of muscle contractions in the second limb;
    a second compression apparatus embedded in the second garment for applying an external compression to the second limb of the user; and
    at least one of a second processor or a second controller coupled to the second compression apparatus configured to control the second compression apparatus to apply pressure, according to a second compression sequence, to a muscle of the second limb based on the real-time measurements of the cardiac cycle of the user associated with the second limb and the real-time measurements of the muscle contractions of the second limb wherein the second compression sequence is synchronized to commence when both the local blood flow at the second limb is in the diastolic phase and the muscle in the second limb is in a non-contracted state.

15. A method comprising:
    sensing, by a cardiac cycle sensor, real-time measurements regarding a cardiac cycle having a diastolic phase and systolic phase of a user,
    sensing, by a muscle activity sensor, real-time measurements of muscle contractions in a limb of the user;
    applying compression, by a compression apparatus, to a muscle in the limb of the user; and
    controlling the compression, by a processor coupled to the compression apparatus, according to a compression sequence, based on the real-time measurements of the cardiac cycle of the user and the real-time measurements of the muscle contractions wherein the compression sequence is synchronized to commence when both a local blood flow at the limb is in the diastolic phase and the muscle is in a non-contracted state.

16. The method set forth in claim 15, further comprising:
    sensing, by a pressure sensor, an amount of pressure applied during compression wherein the compression is varied in response to the sensed pressure.

17. The method set forth in claim 15, wherein:
    the compression apparatus comprises a plurality of compression segments, each compression segment comprising an artificial muscle integrated in a wearable garment which in response to an electrical stimulus supplied by the processor causes a compression state or an expansion state.

18. The method set forth in claim 17, wherein the compression sequence activates the plurality of compression segments beginning at a first compression segment of the plurality of compression segments being furthest from the heart of the user and concludes with a last compression segment of the plurality of compression segments corresponding to a location on the limb closest to the heart of the user, during the diastolic phase of the local blood flow.

19. The method set forth in claim 15, wherein each compression segment comprises a plurality of active layers being in electrical communication with the processor, the plurality of active layers being a pressure sensor, the artificial muscle and the muscle activity sensor.

20. The method set forth in claim 15, further comprising:
- sensing, by a second cardiac cycle sensor, real-time measurements regarding a cardiac cycle having a diastolic phase and systolic phase of the user in a second limb;
- sensing, by a second muscle activity sensor, real-time measurements of muscle contractions in the second limb;
- applying compression, by a second compression apparatus, to the second limb of the user; and
- controlling, by a second processor, the compression by the second compression apparatus, according to a second compression sequence, to a muscle of the second limb based on the real-time measurements of the cardiac cycle of the user associated with the second limb and the real-time measurements of the muscle contractions of the second limb wherein the second compression sequence is synchronized to commence when both the local blood flow at the second limb is in the diastolic phase and the muscle in the second limb is in a non-contracted state.

* * * * *